(12) United States Patent
Endo et al.

(10) Patent No.: US 9,035,941 B2
(45) Date of Patent: May 19, 2015

(54) IMAGE PROCESSING APPARATUS AND IMAGE PROCESSING METHOD

(75) Inventors: Takaaki Endo, Urayasu (JP); Kiyohide Satoh, Kawasaki (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 303 days.

(21) Appl. No.: 13/257,720

(22) PCT Filed: Mar. 10, 2010

(86) PCT No.: PCT/JP2010/054465
§ 371 (c)(1),
(2), (4) Date: Sep. 20, 2011

(87) PCT Pub. No.: WO2010/113633
PCT Pub. Date: Oct. 7, 2010

(65) Prior Publication Data
US 2012/0007863 A1 Jan. 12, 2012

(30) Foreign Application Priority Data
Mar. 31, 2009 (JP) ................................. 2009-087835

(51) Int. Cl.
*G06T 15/00* (2011.01)
*A61B 8/13* (2006.01)
(Continued)

(52) U.S. Cl.
CPC . *A61B 8/13* (2013.01); *G06T 19/00* (2013.01); *G06T 17/20* (2013.01); *A61B 8/42* (2013.01); *A61B 8/483* (2013.01)

(58) Field of Classification Search
CPC ............ A61B 8/13; A61B 8/42; A61B 8/483; G06T 19/00; G06T 17/20; G06T 17/00
See application file for complete search history.

(56) References Cited

U.S. PATENT DOCUMENTS

| 5,953,013 A | * | 9/1999 | Shimizu | ......................... 345/419 |
| 2002/0173720 A1 | * | 11/2002 | Seo et al. | ....................... 600/437 |

(Continued)

FOREIGN PATENT DOCUMENTS

| JP | 7-047066 A | 2/1995 |
| JP | 11-056752 A | 3/1999 |

(Continued)

OTHER PUBLICATIONS

Wein et al., "Simulation and fully automatic multimodal registration of medical ultrasound," Proc. MICCAI'07, vol. 1, pp. 136-143, 2007.

(Continued)

*Primary Examiner* — James A Thompson
*Assistant Examiner* — Tapas Mazumder
(74) *Attorney, Agent, or Firm* — Carter, DeLuca, Farrell & Schmidt, LLP

(57) ABSTRACT

Based on the position and orientation information of an ultrasonic probe, an image generation unit acquires, from three-dimensional volume data, an image of a slice corresponding to a tomographic image of an object obtained by the ultrasonic probe. An image composition unit composes the image of the slice with the tomographic image to generate and output a composite image. In this composition, a region of the tomographic image is specified as an unclear image sensing region, and the image in the unclear image sensing region is replaced with the image in a region of the image of the slice corresponding to the unclear image sensing region, thereby composing the tomographic image with the image of the slice.

17 Claims, 23 Drawing Sheets

(51) Int. Cl.
  *G06T 17/20* (2006.01)
  *A61B 8/00* (2006.01)
  *A61B 8/08* (2006.01)
  *G06T 19/00* (2011.01)

(56) References Cited

U.S. PATENT DOCUMENTS

| | | | |
|---|---|---|---|
| 2006/0142649 A1* | 6/2006 | Sato | 600/310 |
| 2007/0073114 A1* | 3/2007 | Gundel | 600/300 |
| 2008/0219540 A1* | 9/2008 | Ter Mors | 382/132 |
| 2009/0034837 A1* | 2/2009 | Kato et al. | 382/167 |

FOREIGN PATENT DOCUMENTS

| | | |
|---|---|---|
| JP | 2003-010186 A | 1/2003 |
| JP | 2005-319199 A | 11/2005 |
| JP | 2005-349215 A | 12/2005 |
| JP | 3871747 B | 1/2007 |
| JP | 2008-054800 A | 3/2008 |
| JP | 2008-142413 A | 6/2008 |
| JP | 2010-233961 A | 10/2010 |

OTHER PUBLICATIONS

Fenster, "3-Dimensional Ultrasound Imaging," Imaging Economics, 2004.
Fenster et al., "Three-Dimensional Ultrasound Imaging," Institute of Physics Publishing, Phys. Med. Biol. 46, R67-R99, 2001.
Tuthill et al., "Automated three-dimensional US frame positioning computed from elevational speckle decorrelation," Radiology, vol. 209, pp. 575-582, 1998.
Wein et al., "Automatic registration and fusion of ultrasound with CT for radiotherapy," Proc. MICCAI 2005, vol. 2, pp. 303-311, 2005.
Treece et al., "Correction of probe pressure artifacts in freehand 3D ultrasound," Medical Image Analysis, vol. 6, No. 3, pp. 199-214, 2002.
Fukuoka, "Computer-Aided Diagnosis System on Breast Ultrasound", Japanese Journal of Radiological Technology, vol. 63, No. 12, pp. 1429-1434, 2007.

\* cited by examiner

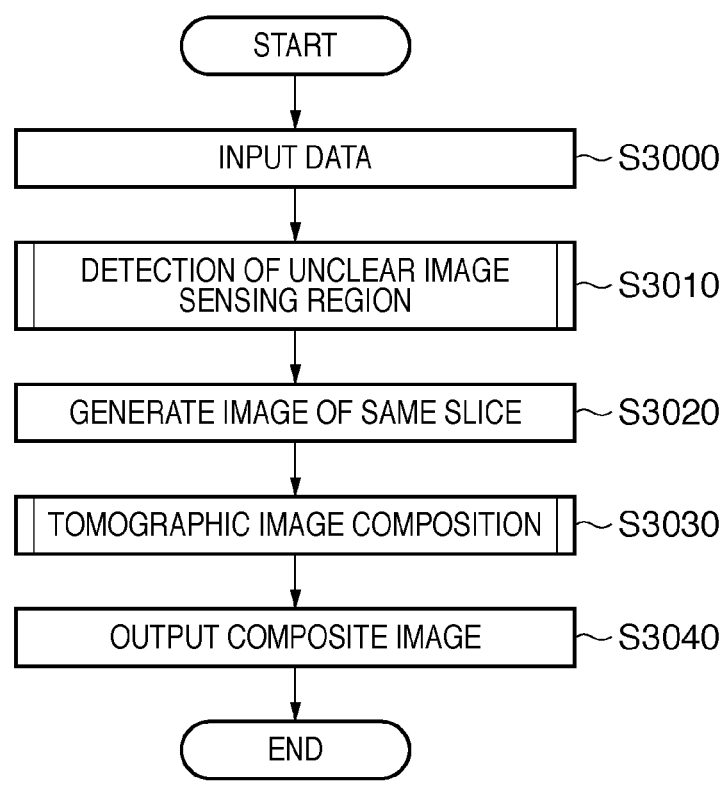
F I G. 3

F I G. 26
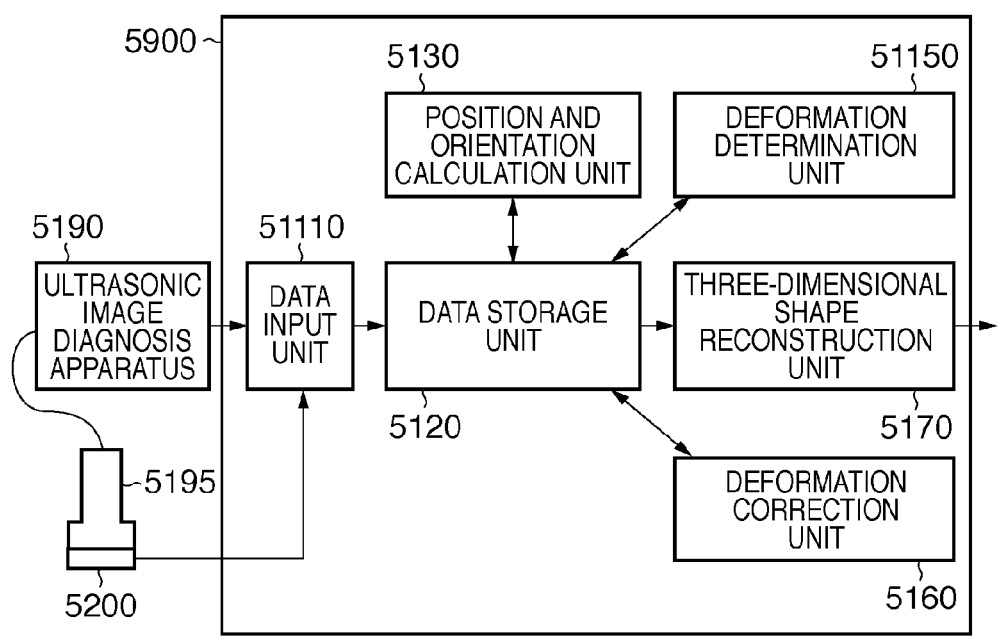
F I G. 27
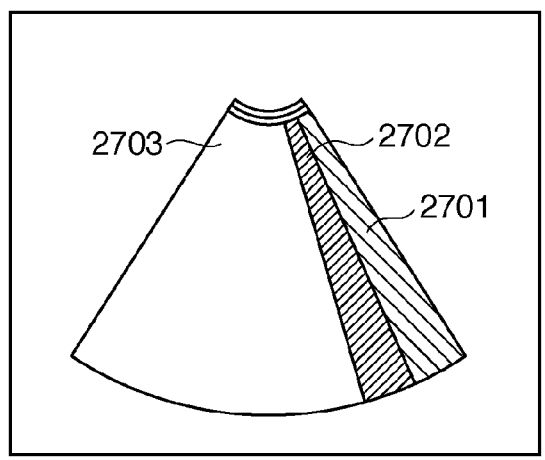

IMAGE PROCESSING APPARATUS AND IMAGE PROCESSING METHOD

TECHNICAL FIELD

The present invention relates to a technique of processing an image obtained by a medical image collection apparatus (modality) such as an ultrasonic image diagnosis apparatus, magnetic resonance imaging apparatus (MRI), X-ray computerized tomography apparatus (X-ray CT), or optical coherence tomography (OCT).

BACKGROUND ART

In the medical field, a doctor displays, on a monitor, a medical image obtained by sensing an object and diagnostically interprets the displayed medical image, thereby observing the state or time-rate change of a morbid portion. Many of the medical images are tomographic images inside the object. Examples of medical image collection apparatuses (modalities) for obtaining a tomographic image are an ultrasonic image diagnosis apparatus, magnetic resonance imaging apparatus (MRI), X-ray computerized tomography apparatus (X-ray CT), and optical coherence tomography (OCT).

It is difficult to grasp the state of an unclear image sensing region existing in an obtained tomographic image just by observing individual tomographic images (obtained tomographic images) obtained by these modalities.

The unclear image sensing region will be described here with reference to FIG. 17. The unclear image sensing region is an unclear region in the image sensing region of an obtained tomographic image where the luminance is higher or lower than usual. For example, when an ultrasonic image diagnosis apparatus is used as the medical image collection apparatus for obtaining a tomographic image, a shadow region or a posterior echo region corresponds to the unclear image sensing region. The shadow region is a region where the state inside the object is not visualized in the obtained tomographic image because the ultrasonic probe serving as an image sensing unit is not in appropriate contact with the object surface. Note that if the ultrasonic probe is not in contact with the object surface at all, the entire image sensing region of the obtained tomographic image is detected as the shadow region. The posterior echo region is an unclear region in the image sensing region of an obtained tomographic image where the luminance is higher or lower than usual because of the influence of a tumor or the like inside the object. Note that in the following description, the outside of the image sensing region of an obtained tomographic image is not included in the unclear image sensing region.

Non-patent reference 1 (W. Wein, A. Khamene, D-A. Clevert, O. Kutter, and N. Navab, "Simulation and fully automatic multimodal registration of medical ultrasound," Proc. MICCAI'07, vol. 1, pp. 136-143, 2007.) discloses a method of obtaining a tomographic image using a given modality, generating an image of the same slice based on three-dimensional geometric volume data acquired by another modality, and displaying both images in a superimposed manner. According to this method, even if the obtained tomographic image contains an unclear image sensing region, it is possible to grasp the state of the unclear image sensing region as far as a corresponding region is visualized in the tomographic image (generated tomographic image) generated based on the three-dimensional geometric volume data acquired by another modality. Patent reference 1 (Japanese Patent No. 3871747) discloses a method of displaying an obtained tomographic image and a generated tomographic image side by side. This method also allows to obtain the same effect as non-patent reference 1.

It is difficult to grasp the three-dimensional shape or range of a morbid portion only by observing individual tomographic images obtained by the above-described modalities. There is an attempt to reconstruct three-dimensional shape data from a tomographic image group. If the three-dimensional shape data has been reconstructed, analysis or display is done based on the reconstructed data, thereby easily grasping the three-dimensional shape or range of a morbid portion.

A medical image collection apparatus such as an MRI, X-ray CT, or OCT obtains a tomographic image group at an equal interval. It is therefore possible to easily reconstruct three-dimensional shape data by simply stacking the tomographic images. However, an ultrasonic image diagnosis apparatus normally performs image sensing while a doctor or a technician holds an ultrasonic probe in hand and freely moves it. For this reason, the position of the space based on the human body, which is visualized in each obtained tomographic image, is unknown. An attempt has been made to measure the position and orientation of the ultrasonic probe using an external sensor and obtain the positional relationship between tomographic images, thereby reconstructing three-dimensional shape data (non-patent reference 2 (A. Fenster, "3-Dimensional Ultrasound Imaging," Imaging Economics, 2004)). Another attempt has also been made to estimate the positional relationship between tomographic images based on the correlation between image features in the tomographic images without using any external sensor, thereby reconstructing three-dimensional shape data (non-patent reference 3 (T. A. Tuthill, J. F. Krucker, J. B. Fowlkes, and P. L. Carson, "Automated three-dimensional US frame positioning computed from elevational speckle decorrelation," Radiology, vol. 209, pp. 575-582, 1998.)).

The tomographic image group is obtained while pressing the probe against the object. For this reason, the object deforms due to the pressure of the probe, and the reconstructed three-dimensional shape data is distorted.

To prevent this, a deformation-free object shape is acquired separately, and deformation is corrected based on it. For example, a method disclosed in non-patent reference 4 (W. Wein, B. Roper, and N. Navab, "Automatic registration and fusion of ultrasound with CT for radiotherapy," Proc. MICCAI 2005, vol. 2, pp. 303-311, 2005.) acquires the deformation-free three-dimensional shape data of an object in advance using X-ray CT, and generates a simulated ultrasonic image based on it. A tomographic image actually obtained by an ultrasonic image diagnosis apparatus is associated with the simulated image based on image information. This enables correction of deformation.

Still another attempt has been made to estimate and correct the object deformation amount caused by the probe pressure. For example, non-patent reference 5 (G. M. Treece, R. W. Prager, A. H. Gee, and L. Berman, "Correction of probe pressure artifacts in freehand 3D ultrasound," Medical Image Analysis, vol. 6, no. 3, pp. 199-214, 2002.) discloses a method of estimating and correcting, based on an image feature in a tomographic image and the measured value of a position and orientation sensor, the amount of deformation caused by the probe pressure. This method assumes that deformation occurs only in the probe pressure application direction. The deformation amount corresponding to the depth from the body surface of each tomographic image is estimated and corrected by calculating the correlation between the horizontal lines of tomographic images at adjacent image sensing times. At this time, the correction is done by adjusting the estimated value of the deformation amount of each tomographic image such that the estimated values of the deformation amounts and the measured values of the position and orientation sensor at the image sensing start and end times are consistent.

However, in the method of non-patent reference 1, a clearly sensed region (clear image sensing region) and an unclear image sensing region in an obtained tomographic image are not explicitly discriminated. Hence, the generated tomographic image covers the clear image sensing region as well and impedes observation of the clear image sensing region. Even if, for example, a biopsy cannula is included in the clear image sensing region, the cannula is hard to view.

In the method of patent reference 1, the doctor needs to complement the unclear image sensing region in the obtained tomographic image by observing the corresponding region in the generated tomographic image. At this time, it is impossible to accurately determine the correspondence between the unclear image sensing region in the obtained tomographic image and a region in the generated tomographic image. This still makes it difficult to grasp the state of the unclear image sensing region.

The method of non-patent reference 4 independently requires a medical image collection apparatus such as X-ray CT to obtain the reference object shape without deformation caused by the probe pressure. That is, it is impossible to reconstruct a three-dimensional shape without deformation from only a tomographic image group obtained by an ultrasonic image diagnosis apparatus.

In the method of non-patent reference 5, the measured value obtained by the position and orientation sensor represents the position and orientation of the deformed body surface, and the correct value of the amount of deformation caused by the probe pressure cannot be found. This makes it impossible to accurately correct the deformation and obtain the reference object shape without deformation.

DISCLOSURE OF INVENTION

The present invention has been made in consideration of the above-described problems, and provides a technique of complementing an unclear image sensing region in an obtained tomographic image based on three-dimensional volume data.

It is another object of the present invention to provide a technique of reconstructing three-dimensional shape data with a little distortion from a tomographic image group.

According to the first aspect of the present invention, an image processing apparatus comprising: an unit which acquires a tomographic image of an object obtained by an image sensing unit; an unit which acquires position and orientation information of the image sensing unit; an unit which acquires three-dimensional volume data of the object; an unit which acquires an image of a slice corresponding to the tomographic image from the three-dimensional volume data based on the position and orientation information; a generation unit which generates a composite image by composing the image of the slice with the tomographic image; and an output unit which outputs the composite image, wherein the generation unit specifies a region as an unclear image sensing region of the tomographic image, and composes the tomographic image with the image of the slice by replacing an image in the unclear image sensing region with an image in a region of the image of the slice corresponding to the unclear image sensing region.

According to the second aspect of the present invention, an image processing method comprising: a step of acquiring a tomographic image of an object obtained by an image sensing unit; a step of acquiring position and orientation information of the image sensing unit; a step of acquiring three-dimensional volume data of the object; a step of acquiring an image of a slice corresponding to the tomographic image from the three-dimensional volume data based on the position and orientation information; a generation step of generating a composite image by composing the image of the slice with the tomographic image; and an output step of outputting the composite image, wherein in the generation step, a region as an unclear image sensing region of the tomographic image is specified, and the tomographic image is composed with the image of the slice by replacing an image in the unclear image sensing region with an image in a region of the image of the slice corresponding to the unclear image sensing region.

According to the third aspect of the present invention, an image processing apparatus comprising: an acquisition unit which time-serially acquires tomographic images of an object obtained by an image sensing unit; a determination unit which determines whether a tomographic image acquired by the acquisition unit is a tomographic image obtained in a state in which the image sensing unit is in contact with the object; a correction unit which corrects deformation of, out of tomographic image groups obtained in a state in which the image sensing unit is in contact with the object, a tomographic image group other than a tomographic image obtained immediately after the contact and a tomographic image obtained immediately before cancel of the contact; and a generation unit which generates three-dimensional shape data of the object based on the tomographic image group corrected by the correction unit.

According to the fourth aspect of the present invention, an image processing apparatus comprising: an acquisition unit which time-serially acquires tomographic images of an object obtained by an image sensing unit and position and orientation information of the image sensing unit; a determination unit which determines whether a tomographic image acquired by the acquisition unit is a tomographic image obtained in a state in which the image sensing unit is in contact with the object; and a generation unit which generates three-dimensional shape data of the object using the position and orientation information immediately before and immediately after the contact and the position and orientation information immediately before and immediately after cancel of the contact.

According to the fifth aspect of the present invention, an image processing method comprising: an acquisition step of time-serially acquiring tomographic images of an object obtained by an image sensing unit; a determination step of determining whether a tomographic image acquired in the acquisition step is a tomographic image obtained in a state in which the image sensing unit is in contact with the object; a correction step of correcting deformation of, out of tomographic image groups acquired in the acquisition step, a tomographic image group other than a tomographic image obtained immediately after the contact and a tomographic image obtained immediately before cancel of the contact; and a generation step of generating three-dimensional shape data of the object based on the tomographic image group corrected in the correction step.

According to the sixth aspect of the present invention, an image processing method comprising: an acquisition step of time-serially acquiring tomographic images of an object obtained by an image sensing unit and position and orientation information of the image sensing unit; a determination step of determining whether a tomographic image acquired in the acquisition step is a tomographic image obtained in a state in which the image sensing unit is in contact with the object;

and a generation step of generating three-dimensional shape data of the object using the position and orientation information immediately before and immediately after the contact and the position and orientation information immediately before and immediately after cancel of the contact.

Further features of the present invention will become apparent from the following description of exemplary embodiments with reference to the attached drawings.

BRIEF DESCRIPTION OF DRAWINGS

FIG. 3 is a flowchart illustrating the operation of the image processing apparatus according to the first embodiment;

FIG. 26 is a block diagram showing an example of the functional arrangement of an image processing apparatus according to the 10th embodiment; and FIG. 27 is a view for explaining a contact determination method according to the third modification of other embodiments.

BEST MODE FOR CARRYING OUT THE INVENTION

The embodiments of the present invention will now be described with reference to the accompanying drawings. Note that the embodiments to be explained below are detailed embodied examples of the present invention and are included in detailed examples of the arrangements described in the appended claims.

First Embodiment

An image processing apparatus according to this embodiment detects an unclear image sensing region in an obtained tomographic image and complements the detected unclear image sensing region based on three-dimensional volume data. Note that in this embodiment, a case will be described in which a shadow region is handled as an unclear image sensing region, and three-dimensional volume data is handled as three-dimensional image data. The embodiment will be explained below.

Figure 1:
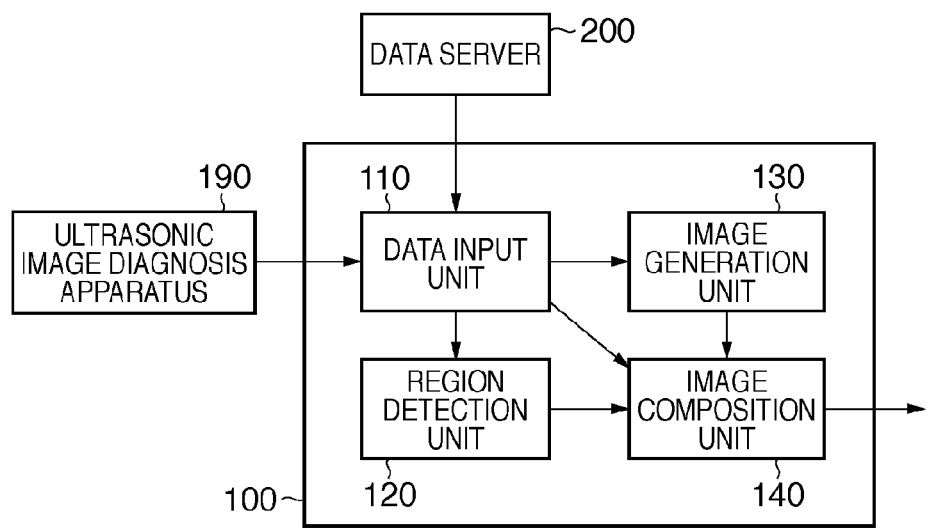
FIG. 1 is a block diagram showing an example of the functional arrangement of an image processing apparatus according to the first embodiment.

The arrangement of the image processing apparatus according to the embodiment and its peripheral devices will be described first with reference to FIG. 1. As shown in FIG. 1, an image processing apparatus 100 according to this embodiment includes a data input unit 110, region detection unit 120, image generation unit 130, and image composition unit 140. An ultrasonic image diagnosis apparatus 190 serving as a medical image collection apparatus for obtaining a tomographic image is connected to the image processing apparatus 100. A data server 200 configured to hold the three-dimensional volume data of an object is also connected to the image processing apparatus 100.

The ultrasonic image diagnosis apparatus 190 obtains a tomographic image of an object in real time. The tomographic image (obtained tomographic image) obtained by the ultrasonic image diagnosis apparatus 190 is input to the image processing apparatus 100 via the data input unit 110.

Normally, a doctor or a technician senses an object while holding an ultrasonic probe serving as the image sensing unit (not shown) of the ultrasonic image diagnosis apparatus 190 in hand and freely moving the probe. However, since the position of the space based on the object, which is visualized in the obtained tomographic image, is unknown, a position and orientation sensor (not shown) is attached to the image sensing unit to measure the position and orientation of the image sensing unit. The position and orientation sensor is formed from, e.g., FASTRAK available from Polhemus, U.S.A. Note that the position and orientation sensor can have any design if it can measure the position and orientation of the image sensing unit. In all acquisition methods, position and orientation information representing the position and orientation of the image sensing unit is input to the image processing apparatus 100 via the data input unit 110. The position and orientation of the image sensing unit are represented by a position and orientation on, for example, a reference coordinate system (a coordinate system whose origin is defined at one point on a space based on an object, and whose X-, Y-, and Z-axes are defined as three axes that cross at right angles at that origin). Note that the position and orientation of the image sensing unit may be input by the operator using a keyboard or mouse (not shown).

The data server 200 holds the three-dimensional volume data of the same object as that of the obtained tomographic image. The three-dimensional volume data is, for example, reconstructed in advance from a tomographic image group obtained by previously causing the ultrasonic image diagnosis apparatus 190 to sense the object. For example, according to the method disclosed in non-patent reference 2, the position and orientation of the image sensing unit are measured using the position and orientation sensor, and the positional relationship between tomographic images is obtained, thereby reconstructing three-dimensional volume data.

Note that the three-dimensional volume data is expressed on the above-described reference coordinate system. The three-dimensional volume data of the object is input to the image processing apparatus 100 via the data input unit 110.

An unclear image sensing region (in this case, including a posterior echo region) in a tomographic image obtained by sensing the object from a given direction is sometimes a clear image sensing region in another tomographic image obtained by sensing the object from another direction. In this case, use of a tomographic image group obtained by sensing the object from a plurality of directions allows to reconstruct three-dimensional volume data in which the unclear image sensing region is complemented to some extent. As a consequence, a generated tomographic image in which the unclear image sensing region is complemented to some extent can be obtained. The "generated tomographic image" is a tomographic image generated based on three-dimensional volume data acquired by another modality, as described above. The units of the image processing apparatus 100 will be explained next.

The data input unit 110 converts the obtained tomographic image input from the ultrasonic image diagnosis apparatus 190 into digital data as needed, and outputs it to the region detection unit 120 and the image composition unit 140. The data input unit 110 also outputs, to the image generation unit 130, three-dimensional volume data concerning the same object as that of the obtained tomographic image, which is input from the data server 200. Based on the position and orientation information of the image sensing unit input from the ultrasonic image diagnosis apparatus 190 and the "position and orientation information of the obtained tomographic image on the image sensing unit coordinate system", which is calculated and held in advance, the data input unit 110 obtains position and orientation information of the obtained tomographic image on the reference coordinate system. The data input unit 110 outputs, to the image generation unit 130 of the succeeding stage, the obtained "position and orientation information of the obtained tomographic image on the reference coordinate system". The image sensing unit coordinate system is a coordinate system whose origin is defined at one point on the image sensing unit, and whose X-, Y-, and Z-axes are defined as three axes that cross at right angles at that origin.

The region detection unit 120 detects the shadow region in the obtained tomographic image input from the data input unit 110, and outputs data representing the detected region to the image composition unit 140. In this embodiment, a mask image is used as the data representing the shadow region. The mask image has the same size as that of the obtained tomographic image and assigns different pixel values to the shadow region and regions other than it.

The image generation unit 130 generates a tomographic image using the three-dimensional volume data input from the data input unit 110 and the position and orientation information of the obtained tomographic image on the reference coordinate system, and outputs the generated tomographic image to the image composition unit 140.

Using the obtained tomographic image input from the data input unit 110, the mask image input from the region detection unit 120, and the generated tomographic image input from the image generation unit 130, the image composition unit 140 composes the generated tomographic image with the shadow region of the obtained tomographic image. The image composition unit 140 outputs the composite image obtained by the composition process to an external device.

Note that at least some of the data input unit 110, region detection unit 120, image generation unit 130, and image composition unit 140 shown in FIG. 1 may be implemented as independent devices. Alternatively, the units may be implemented as software applications which are installed in one or a plurality of computers and executed by the CPUs of the computers to implement corresponding functions. In this embodiment, the units (data input unit 110, region detection unit 120, image generation unit 130, and image composition unit 140) are assumed to be implemented as software and installed in a single computer.

Figure 2:
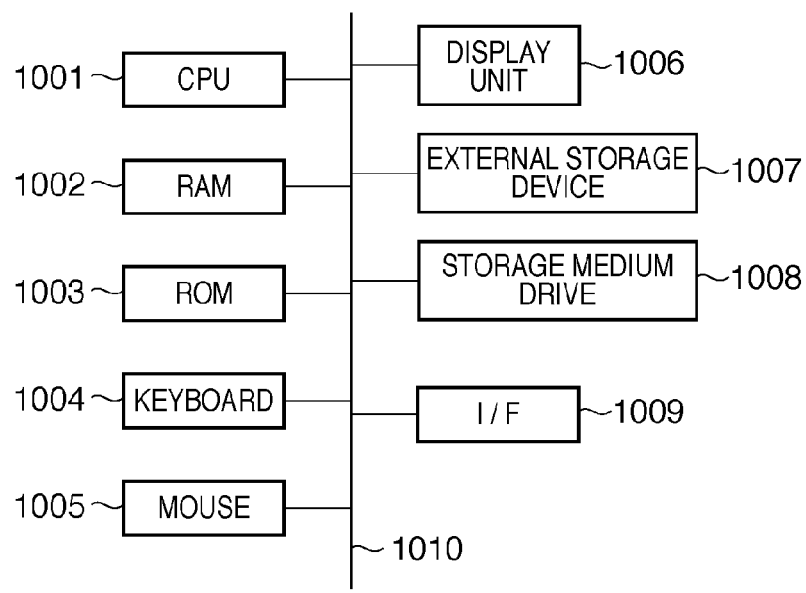
FIG. 2 is a block diagram showing an example of the hardware configuration of a computer.

The hardware configuration of the computer which implements the functions of the data input unit 110, region detection unit 120, image generation unit 130, and image composition unit 140 by executing software will be described with reference to FIG. 2.

A CPU 1001 controls the entire computer using computer programs and data stored in a RAM 1002 and a ROM 1003. The CPU 1001 also implements the functions of the data input unit 110, region detection unit 120, image generation unit 130, and image composition unit 140 by executing software applications corresponding to them.

The RAM 1002 is an example of a computer-readable storage medium and has an area for temporarily storing computer programs and data loaded from an external storage device 1007 or a storage medium drive 1008. The RAM 1002 also has an area for temporarily storing data received from the outside via an I/F 1009 and a work area necessary for the CPU 1001 to perform various kinds of processing.

The ROM 1003 is an example of a computer-readable storage medium and generally stores computer programs and setting data. A keyboard 1004 and a mouse 1005 are used as input devices. The operator can input various instructions to the CPU 1001 by using them.

A display unit 1006 is formed from a CRT, a liquid crystal display, or the like and can display the processing result of the CPU 1001 as an image or characters. For example, the display unit 1006 can display various kinds of medical images such as an obtained tomographic image and a composite image, or a message which should be displayed for image processing.

The external storage device 1007 is a mass information storage device represented by a hard disk drive. The external storage device 1007 stores the OS (Operating System), and programs and data which are used to cause the CPU 1001 to execute each processing to be described later as processing to be executed by the image processing apparatus according to this embodiment. The computer programs include computer programs which cause the CPU 1001 to implement the functions of the data input unit 110, region detection unit 120, image generation unit 130, and image composition unit 140. The data include data to be described below as known information. Under the control of the CPU 1001, the computer programs and data stored in the external storage device 1007 are loaded to the RAM 1002 as needed as the process target of the CPU 1001.

Under the control of the CPU 1001, the storage medium drive 1008 reads out computer programs and data from a storage medium such as a CD-ROM or a DVD-ROM and outputs them to the RAM 1002 or the external storage device 1007.

The I/F 1009 is formed from an analogue video port configured to connect the ultrasonic image diagnosis apparatus 190, a digital input/output port such as IEEE1394, or an Ethernet® port configured to output the information of a composite image or the like to the outside. The data server 200 is connected to the I/F 1009. Data externally input via the I/F 1009 is stored in the RAM 1002. The I/F 1009 implements some functions of the data input unit 110. The above-described constituent elements are connected to each other via a bus 1010.

The operation of the image processing apparatus according to the embodiment will be described next with reference to FIG. 3. Note that in the following explanation, the units shown in FIG. 1 are the entities of processing. In this embodiment, however, the CPU 1001 executes computer programs corresponding to the units, as described above. Hence, the CPU 1001 is the entity of processing in fact.

In step S3000, the data input unit 110 acquires, from the ultrasonic image diagnosis apparatus 190, the obtained tomographic image of an object and the position and orientation information of the image sensing unit of the ultrasonic image diagnosis apparatus 190. The data input unit 110 also acquires the three-dimensional volume data of the object from the data server 200. Based on the position and orientation information of the image sensing unit and the "position and orientation information of the obtained tomographic image on the image sensing unit coordinate system" which is calculated and held in advance, the data input unit 110 obtains the position and orientation information of the obtained tomographic image on the reference coordinate system. The data input unit 110 outputs the obtained tomographic image to the region detection unit 120 and the image composition unit 140 and the three-dimensional volume data and the "position and orientation information of the obtained tomographic image on the image sensing unit coordinate system" to the image generation unit 130.

In step S3010, the region detection unit 120 detects a shadow region serving as an unclear image sensing region from the obtained tomographic image received from the data input unit 110. Note that the process in this step will be described later in detail with reference to the flowchart of FIG. 4.

In step S3020, based on the position and orientation information obtained by the data input unit 110 in step S3000, the image generation unit 130 generates a tomographic image by extracting, from the three-dimensional volume data, an image of the same slice as that of the obtained tomographic image acquired by the data input unit 110. Note that only a portion corresponding to the shadow region in the three-dimensional volume data may be generated as the generated tomographic image.

In step S3030, the image composition unit 140 composes the tomographic image generated in step S3020 with the shadow region in the obtained tomographic image received from the data input unit 110. Note that the process in this step will be described later in detail with reference to the flowchart of FIG. 6.

In step S3040, the image composition unit 140 outputs the composite image obtained by the composition process in step S3030 to an external device via the I/F 1009. Alternatively, the composite image is stored in RAM 1002 so as to be available for another application.

The shadow region in the obtained tomographic image is complemented based on the three-dimensional volume data by the above-described processing.

Figure 4:
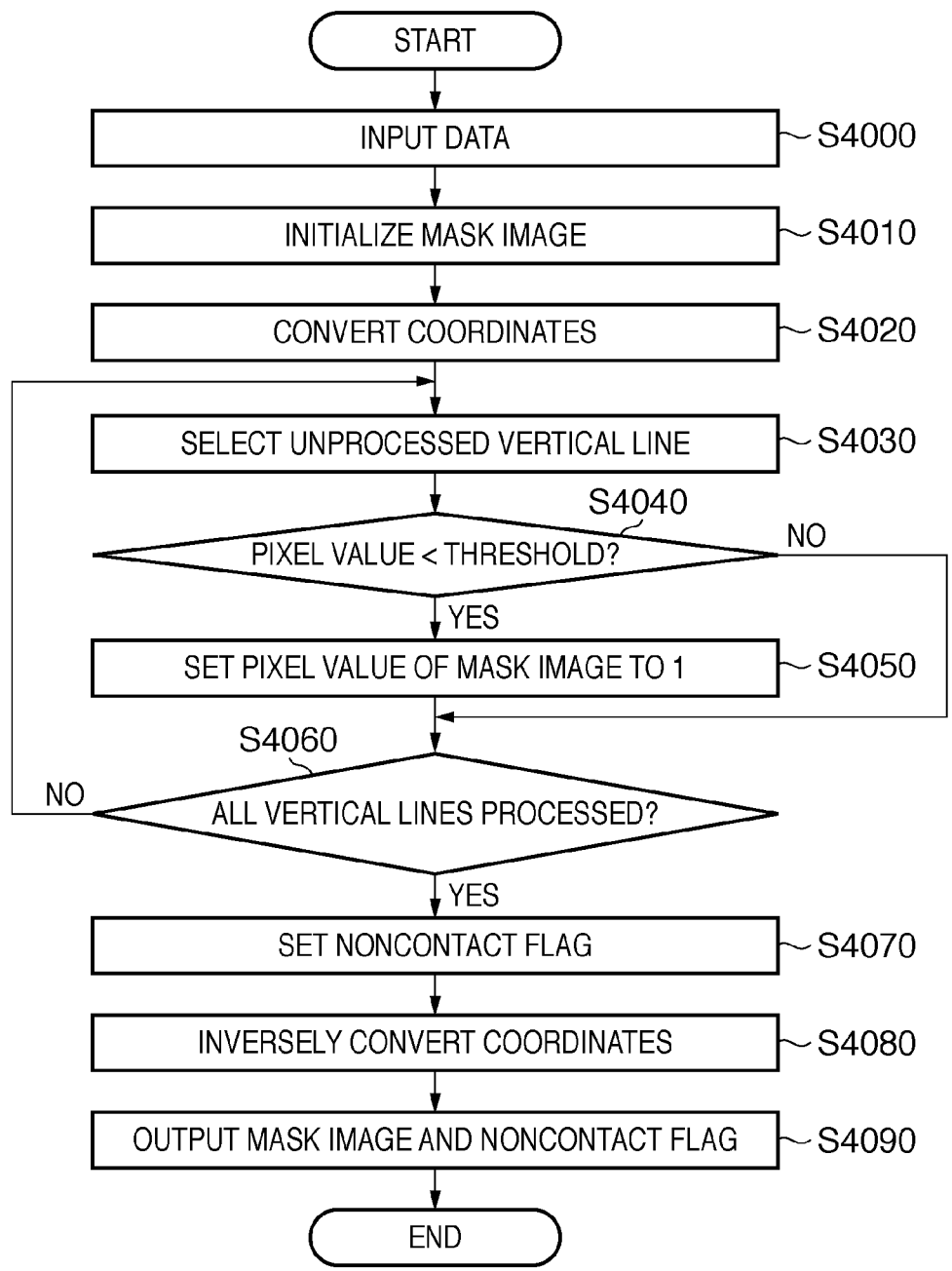
FIG. 4 is a flowchart illustrating the process in step S3010 according to the first embodiment.

Details of the process in step S3010 will be described next with reference to FIG. 4. Note that the processing according to the flowchart of FIG. 4 is implemented by causing the CPU 1001 to execute a computer program that implements the functions of the region detection unit 120.

In step S4000, the region detection unit 120 receives the obtained tomographic image from the data input unit 110. In step S4010, the region detection unit 120 generates, as a mask image, an image having the same size as that of the obtained tomographic image received in step S4000. Note that the pixel values of all pixels of the mask image are set to 0.

Figure 5:
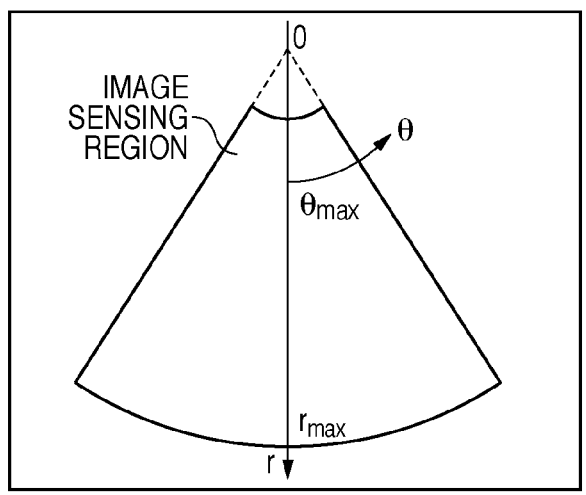
FIG. 5 is a view showing an example of an image sensing region.

In step S4020, the region detection unit 120 converts the image sensing region of the obtained tomographic image into a rectangle, and performs the same conversion for the mask image. For example, when a convex probe is used as the image sensing unit of the ultrasonic image diagnosis apparatus 190, the image sensing region has a fan shape, as shown in FIG. 5. This shape is converted into a rectangle by, e.g., $$x = \frac{r_{max}\theta\tan\theta_{max}}{\theta_{max}} \quad (1)$$

$$y = r$$

where $(r,\theta)$ represents the polar coordinates of the image sensing region of the convex probe as shown in FIG. 5, $r_{max}$ and $\theta_{max}$ are the maximum values of r and $\theta$ in the image sensing region, respectively, and $(x,y)$ represents the orthogonal coordinates after conversion. Note that when a linear probe is used as the image sensing unit of the ultrasonic image diagnosis apparatus 190, the image sensing region is rectangular, and this step is unnecessary.

In step S4030, the region detection unit 120 selects, as a selected vertical line, an unprocessed vertical line in the rectangle region of the obtained tomographic image. In step S4040, the region detection unit 120 determines whether the pixel values (luminance values) of all pixels of the selected vertical line are smaller than a threshold.

The luminance is not necessarily low near the upper end portion of the image sensing region even if the ultrasonic probe is not in appropriate contact with the object surface. Not to use the upper end portion of the image sensing region, it may be determined whether all pixel values at y-coordinates larger than a predetermined y-coordinate value are smaller than the threshold. If the pixel values of all pixels of the selected vertical line are smaller than the threshold upon determination, the process advances to step S4050. Otherwise, the process advances to step S4060.

Note that the processing of determining whether the region is a shadow region is not limited to the above-described processing. For example, the determination may be done by checking whether the average of the pixel values of all pixels of the selected vertical line are equal to or smaller than a threshold, and the variance of the pixel values is equal to or smaller than a threshold.

In step S4050, the region detection unit 120 sets the pixel values of pixels of a line of the mask image corresponding to the selected vertical line to 1, and advances the process to step S4060.

In step S4060, the region detection unit 120 determines whether all vertical lines have been selected in step S4030. If an unselected vertical line exists upon determination, the process returns to step S4030. If all vertical lines have been selected, the process advances to step S4070.

In step S4070, the region detection unit 120 determines whether the pixel values of the mask image at all pixel positions in the rectangle region have been set to 1. If not all pixel values have been set to 1 upon determination, a probe noncontact flag representing whether the ultrasonic probe is not in contact with the object surface at all is set to 0. On the other hand, if all pixel values have been set to 1, the probe noncontact flag is set to 1.

In step S4080, the region detection unit 120 performs inverse conversion of equations (1) for the mask image. Note that when a linear probe is used as the image sensing unit of the ultrasonic image diagnosis apparatus 190, this step is unnecessary.

In step S4090, the region detection unit 120 outputs, to the image composition unit 140, the mask image representing the shadow region and the probe noncontact flag obtained by the processing in step S4000 to S4080.

The above-described processing allows to detect the shadow region from the obtained tomographic image. The detected shadow region is reflected on the mask image as a region formed from a pixel group having pixel values "1".

Figure 6:
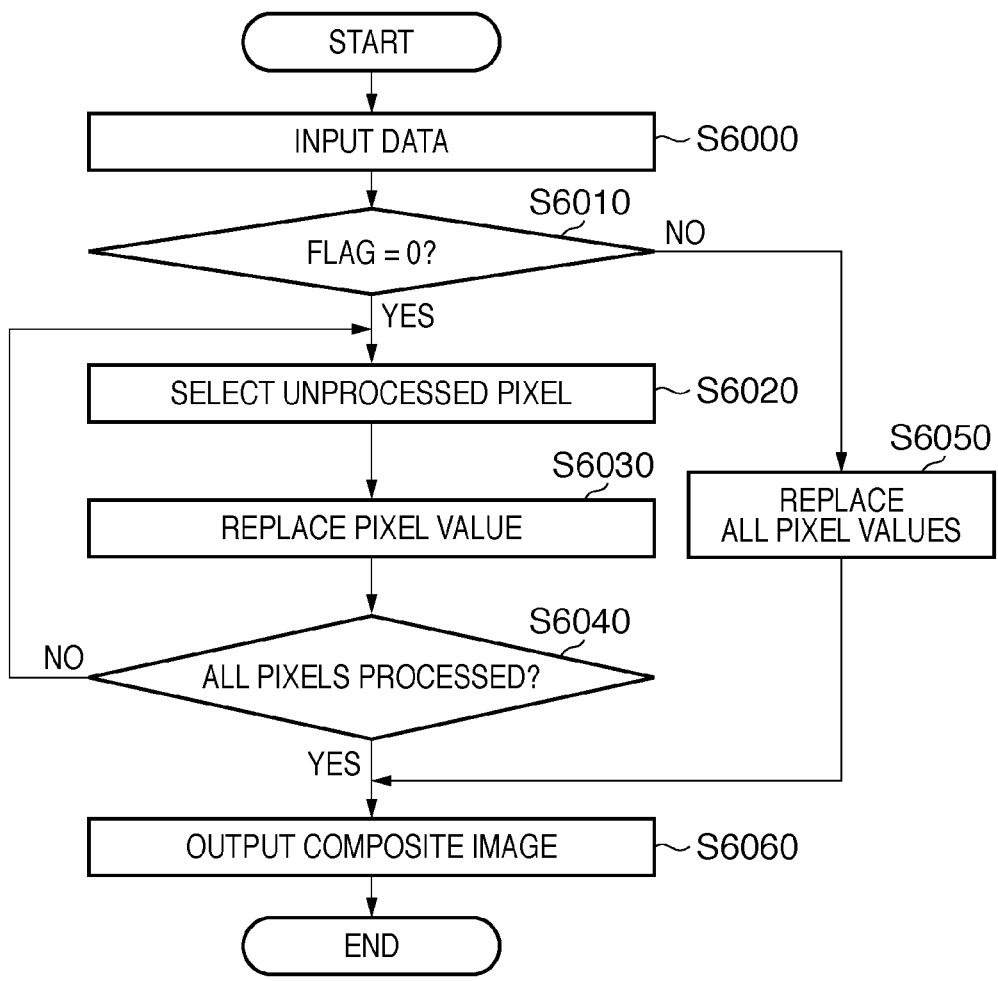
FIG. 6 is a flowchart illustrating the process in step S3030 according to the first embodiment.

Details of the process in step S3030 will be described next with reference to FIG. 6. Note that the processing according to the flowchart of FIG. 6 is implemented by causing the CPU 1001 to execute a computer program that implements the functions of the image composition unit 140.

In step S6000, the image composition unit 140 receives the obtained tomographic image from the data input unit 110 and the mask image representing the shadow region and the probe noncontact flag from the region detection unit 120. The image composition unit 140 also receives the generated tomographic image from the image generation unit 130.

In step S6010, the image composition unit 140 determines whether the probe noncontact flag is 0 or 1. If the probe noncontact flag is 0 upon determination, the process advances to step S6020. If the probe noncontact flag is 1 upon determination, the process advances to step S6050.

In step S6020, the image composition unit 140 selects, as a selected pixel, an unselected pixel in a region, i.e., the shadow region (unclear image sensing region) of the obtained tomographic image corresponding to the region with the pixel value "1" in the mask image.

In step S6030, the image composition unit 140 replaces the pixel value of the selected pixel with the pixel value at the corresponding pixel position of the generated tomographic image. In step S6040, the image composition unit 140 determines whether all pixels in the shadow region have been selected in step S6020. If an unselected pixel exists upon determination, the process returns to step S6020. If all pixels in the shadow region have been selected, the process advances to step S6060.

In step S6050, the image composition unit 140 replaces the pixel values of all pixels of the obtained tomographic image with the pixel values at corresponding pixel positions of the generated tomographic image. In step S6060, the image composition unit 140 stores the obtained tomographic image updated by the processing in steps S6000 to S6050 in the RAM 1002 as the composite image of the obtained tomographic image and the generated tomographic image.

The above-described processing enables to compose the shadow region in the obtained tomographic image with the generated tomographic image.

As described above, according to this embodiment, it is possible to compose a shadow region which is an unclear image sensing region in an obtained tomographic image with the image of the same slice as that of a tomographic image generated based on three-dimensional volume data. This allows to complement the unclear image sensing region based on the three-dimensional volume data without impeding observation of a clear image sensing region in the tomographic image.

Second Embodiment

In the first embodiment, a case has been described in which a shadow region is handled as an unclear image sensing region. However, the unclear image sensing region is not limited to the shadow region and may be a posterior echo region. In the second embodiment, a case will be explained in which a posterior echo region is handled as an unclear image sensing region.

This embodiment will be described below regarding only portions different from the first embodiment. Note that the arrangement of an image processing apparatus according to this embodiment is the same as in FIG. 1 except only the functions of a region detection unit 120 and an image composition unit 140.

The region detection unit 120 receives an obtained tomographic image from a data input unit 110. The region detection unit 120 detects a posterior echo region in the obtained tomographic image as an unclear image sensing region, and outputs data representing the detected region to the image composition unit 140. In this embodiment, a mask image representing the posterior echo region is used as the data representing the posterior echo region.

The image composition unit 140 receives the obtained tomographic image output from the data input unit 110, the mask image representing the posterior echo region output from the region detection unit 120, and a generated tomographic image output from an image generation unit 130. Based on these data, the image composition unit 140 composes the posterior echo region of the obtained tomographic image with the generated tomographic image, and outputs the obtained composite image to the outside.

Figure 7:
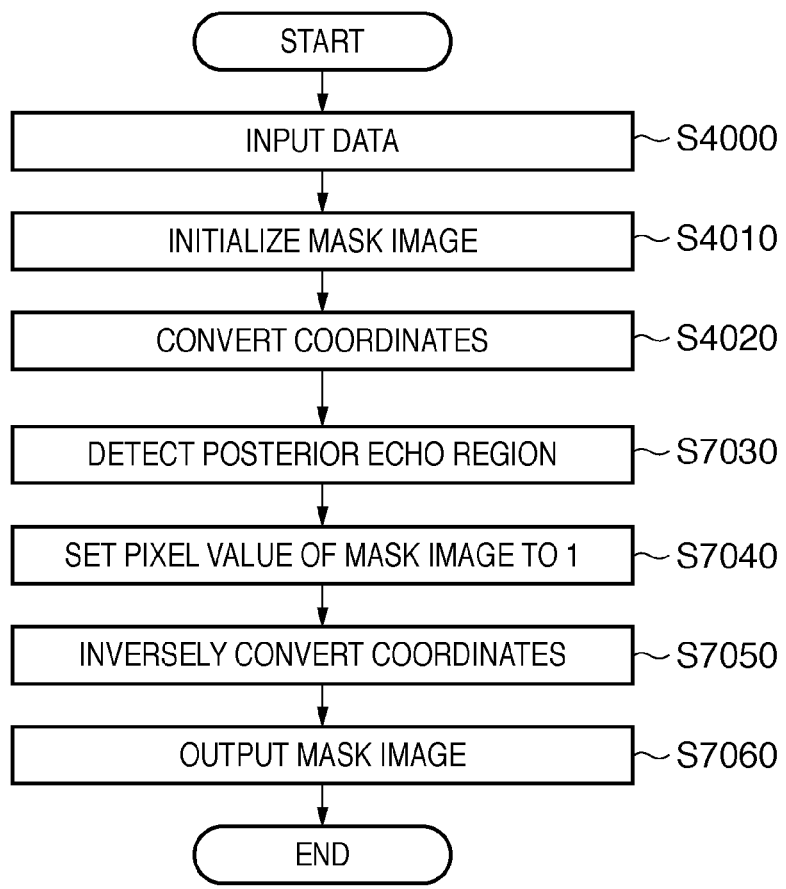
FIG. 7 is a flowchart of the process in step S3010 according to the second embodiment.

Processing to be executed by the region detection unit 120 of this embodiment in step S3010 will be described next with reference to FIG. 7. The same step numbers as in FIG. 4 denote the same processes in FIG. 7, and a description thereof will not be repeated.

In step S7030, the region detection unit 120 detects the posterior echo region of the obtained tomographic image using, e.g., a method disclosed in the following reference.

Fukuoka, "Computer-Aided Diagnosis System on Breast Ultrasound", Japanese Journal of Radiological Technology, vol. 63, no. 12, pp. 1429-1434, 2007.

More specifically, the region detection unit 120 detects a tumor candidate region using a method based on vertical edge detection, and defines the region behind (under) it as a posterior echo region.

In step S7040, the region detection unit 120 sets the pixel values of pixels of a region of the mask image corresponding to the posterior echo region detected in step S7030 to 1, and advances the process to step S7050.

In step S7050, the region detection unit 120 performs inverse conversion of equations (1) for the mask image. Note that when a linear probe is used as the image sensing unit of an ultrasonic image diagnosis apparatus 190, this step is unnecessary.

In step S7060, the region detection unit 120 outputs the mask image representing the posterior echo region obtained by the above-described processing to the image composition unit 140. The above-described processing allows to detect the posterior echo region from the obtained tomographic image.

Figure 8:
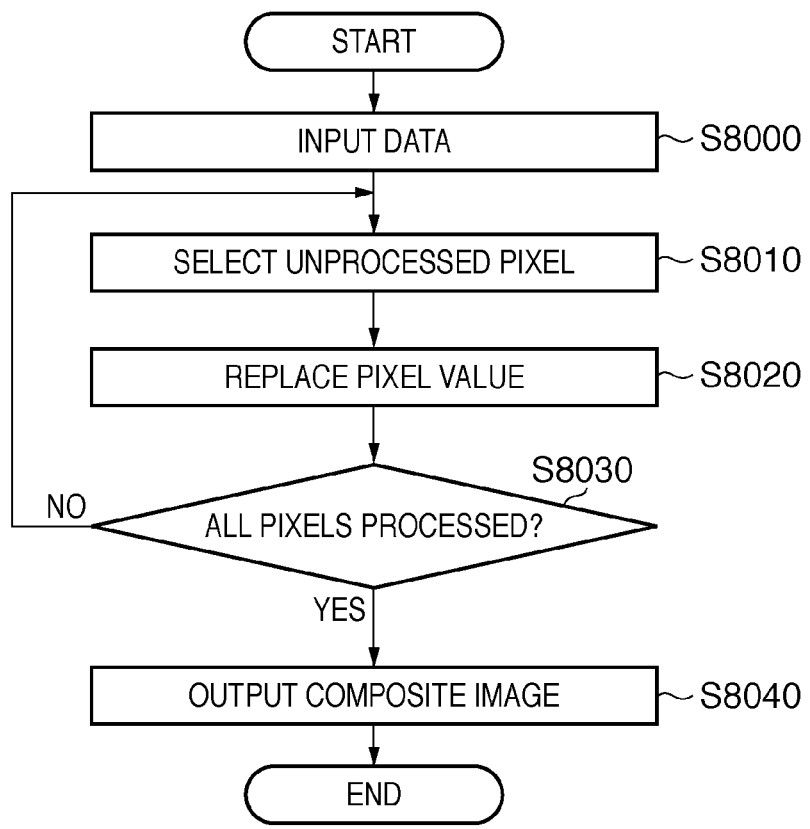
FIG. 8 is a flowchart of the process in step S3030 according to the second embodiment.

Processing to be executed by the image composition unit 140 of this embodiment in step S3030 will be described next with reference to FIG. 8. In step S8000, the image composition unit 140 receives the obtained tomographic image from the data input unit 110 and the mask image representing the posterior echo region from the region detection unit 120. The image composition unit 140 also receives the generated tomographic image from the image generation unit 130.

In step S8010, the image composition unit 140 selects, as a selected pixel, an unselected pixel in a region, i.e., the posterior echo region of the obtained tomographic image corresponding to the region with the pixel value "1" in the mask image.

In step S8020, the image composition unit 140 replaces the pixel value of the selected pixel with the pixel value at the corresponding pixel position of the generated tomographic image. In step S8030, the image composition unit 140 determines whether all pixels in the posterior echo region have been selected in step S8010. If an unselected pixel exists upon determination, the process returns to step S8010. If all pixels in the posterior echo region have been selected, the process advances to step S8040.

In step S8040, the image composition unit 140 outputs the obtained tomographic image updated by the processing in steps S8000 to S8030 as the composite image of the obtained tomographic image and the generated tomographic image. The output destination is not particularly limited, as in the first embodiment. The above-described processing enables to compose the posterior echo region in the obtained tomographic image with the generated tomographic image.

As described above, according to this embodiment, it is possible to compose a posterior echo region which is an unclear image sensing region in a tomographic image with the image of the same slice as that of a tomographic image generated based on three-dimensional volume data. This allows to complement the unclear image sensing region based on the three-dimensional volume data without impeding observation of a clear image sensing region in the tomographic image.

Third Embodiment

In the first embodiment, a case has been described in which a shadow region is handled as an unclear image sensing region. In the second embodiment, a case has been described in which a posterior echo region is handled as an unclear image sensing region. However, the unclear image sensing region is not limited to one of the shadow region and the posterior echo region and may include both of them. In the third embodiment, a case will be explained in which both a shadow region and a posterior echo region are handled as an unclear image sensing region.

This embodiment will be described below regarding only portions different from the first embodiment. Note that the arrangement of an image processing apparatus according to this embodiment is the same as in FIG. 1 except only the functions of a region detection unit 120 and an image composition unit 140.

The region detection unit 120 receives an obtained tomographic image output from a data input unit 110. The region detection unit 120 detects a region that combines a shadow region and a posterior echo region in the obtained tomographic image, and outputs data representing the detected region to the image composition unit 140. In this embodiment, a mask image representing the region that combines the shadow region and the posterior echo region is used as the data representing the region that combines the shadow region and the posterior echo region.

The image composition unit 140 receives the obtained tomographic image output from the data input unit 110, the mask image representing the region that combines the shadow region and the posterior echo region output from the region detection unit 120, and a generated tomographic image output from an image generation unit 130. Based on these data, the image composition unit 140 composes the region that combines the shadow region and the posterior echo region of the obtained tomographic image with the generated tomographic image, and outputs the obtained composite image to the outside.

Figure 9:
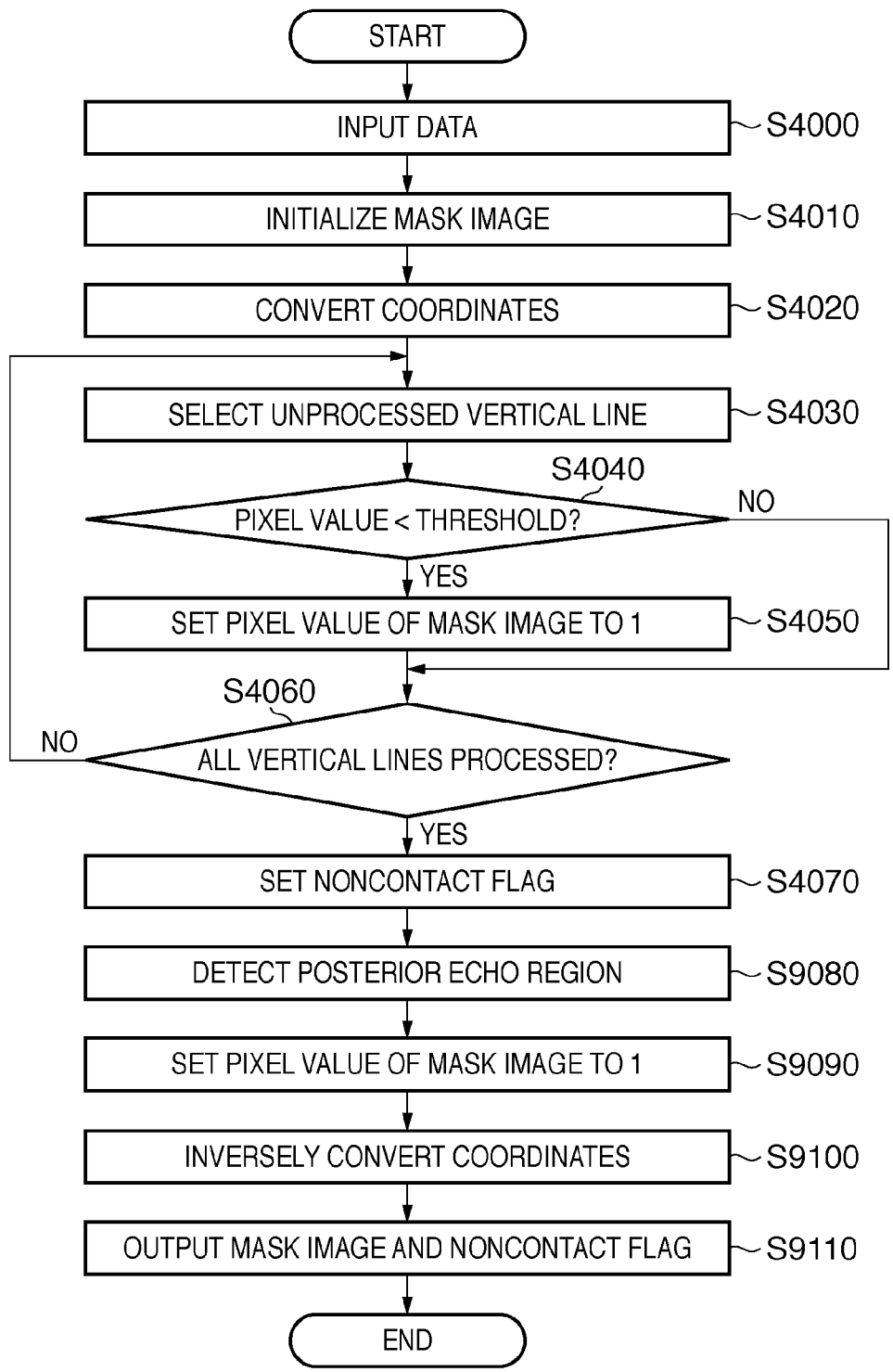
FIG. 9 is a flowchart of the process in step S3010 according to the third embodiment.

Processing to be executed by the region detection unit 120 of this embodiment in step S3010 will be described next with reference to FIG. 9. The same step numbers as in FIG. 4 denote the same processes in FIG. 9, and a description thereof will not be repeated.

In step S9080, the region detection unit 120 detects, using, e.g., the method disclosed in (reference 2) above, the posterior echo region from an image region in the rectangle region of the obtained tomographic image corresponding to the image region with the pixel value "0" in the mask image.

In step S9090, the region detection unit 120 sets the pixel values of pixels of a region of the mask image corresponding to the posterior echo region detected in step S9080 to 1, and advances the process to step S9100.

In step S9100, the region detection unit 120 performs inverse conversion of equations (1) for the mask image. Note that when a linear probe is used as the image sensing unit of an ultrasonic image diagnosis apparatus 190, this step is unnecessary.

In step S9110, the region detection unit 120 outputs, to the image composition unit 140, the mask image representing the region that combines the shadow region and the posterior echo region and a probe noncontact flag obtained by the above-described processing. The above-described processing allows to detect the region that combines the shadow region and the posterior echo region from the obtained tomographic image.

The procedure of processing executed by the image composition unit 140 is the same as that of the processing of the flowchart shown in FIG. 6. The shadow region in the flowchart of FIG. 6 is replaced with the region that combines the shadow region and the posterior echo region.

As described above, according to this embodiment, it is possible to compose a region that combines a shadow region and a posterior echo region, which is an unclear image sensing region in a tomographic image, with the image of the same slice as that of a tomographic image generated based on three-dimensional volume data. This allows to complement the unclear image sensing region based on the three-dimensional volume data without impeding observation of a clear image sensing region in the tomographic image.

Fourth Embodiment

In this embodiment, the image sensing clarity of a region of an obtained tomographic image is calculated using a method corresponding to the property of the unclear image sensing region. In accordance with the image sensing clarity, the obtained tomographic image is composed with a generated tomographic image generated based on three-dimensional volume data. Note that in this embodiment, a case will be described in which a shadow region is handled as an unclear image sensing region, and three-dimensional volume data is handled as three-dimensional image data.

This embodiment will be described below regarding only portions different from the first embodiment. Note that the arrangement of an image processing apparatus according to this embodiment is the same as in FIG. 1 except only the functions of a region detection unit 120 and an image composition unit 140.

In this embodiment, the region detection unit 120 calculates the image sensing clarity of a region in an obtained tomographic image. Note that, for example, defining a region having an image sensing clarity "0" as a clear image sensing region and a region having an image sensing clarity larger than 0 as an unclear image sensing region, image sensing clarity calculation also enables region detection.

Figure 10:
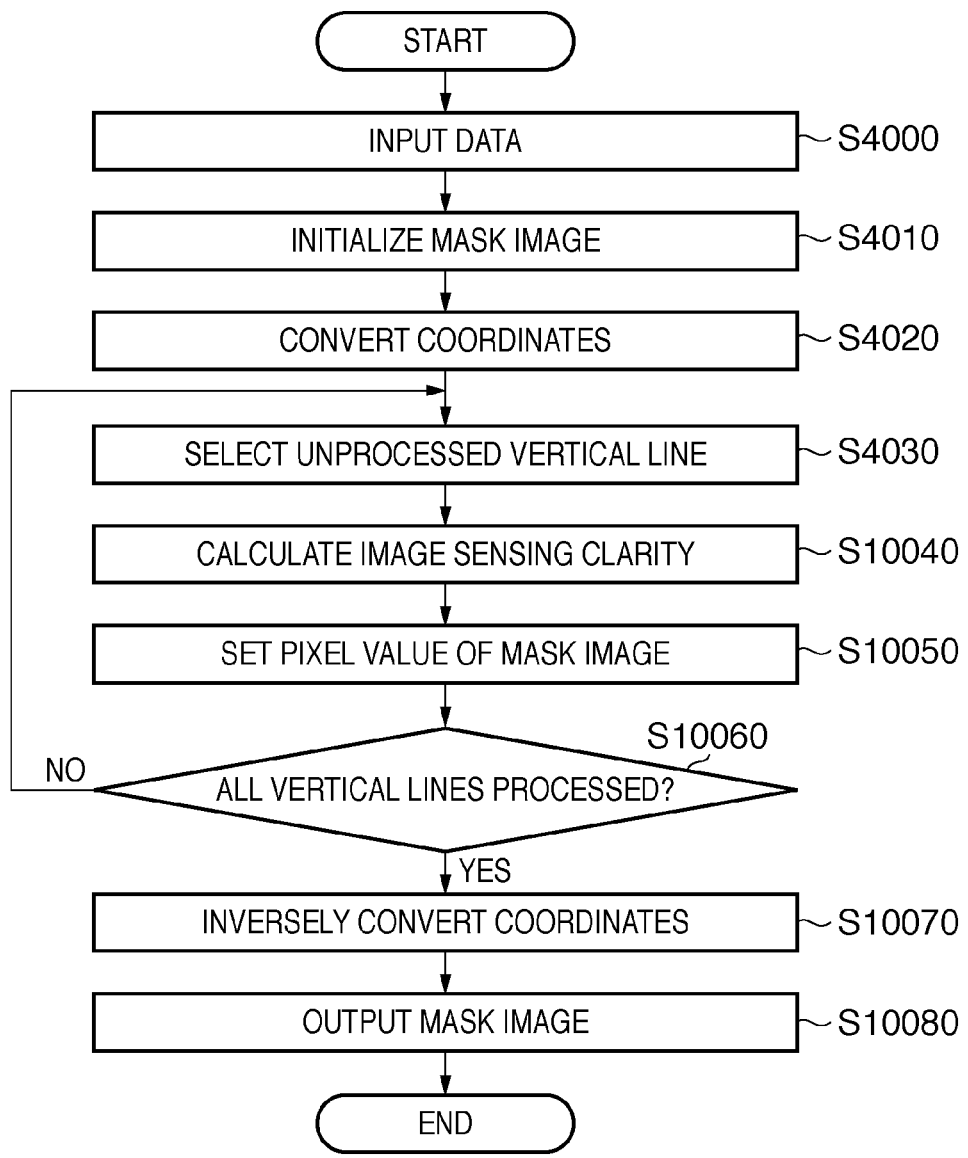
FIG. 10 is a flowchart of the process in step S3010 according to the fourth embodiment.

Processing to be executed by the region detection unit 120 of this embodiment in step S3010 will be described next with reference to FIG. 10. The same step numbers as in FIG. 4 denote the same processes in FIG. 10, and a description thereof will not be repeated.

In step S10040, the region detection unit 120 calculates the shadow region likelihood (image sensing clarity) of a selected vertical line as a value ranging from 0 to 1. For example, an image sensing clarity $R_1$ is calculated by $$R_1 = \sum_{y=y_0}^{y_{max}} \frac{I_0 - I(y)}{I_0} \quad (2)$$

For $R_1 < 0$, $R_1 = 0$ is set, where $y_0$ is a predetermined y-coordinate value, $y_{max}$ is the maximum value of y-coordinate, $I_0$ is the threshold, and $I(y)$ is the luminance value of a pixel having a y-coordinate Y on the selected vertical line. For example, the minimum value of y-coordinate is used as $y_0$. For example, the average value of all pixels of the image sensing region is calculated in advance and used as $I_0$.

In other words, the image sensing clarity is a value obtained by dividing the sum of the differences between the threshold and the pixel values of the pixels of the selected vertical line sequentially selected from the tomographic image by the product of the threshold and the number of pixels of the selected vertical line (when $y_0=0$). When the selected vertical line forms a shadow region, the pixel value $I(y)$ of a pixel included in the selected vertical line is relatively small. As a result, $R_1$ has a large value.

In step S10050, the region detection unit 120 sets the pixel value of each pixel of a line of the mask image corresponding to the selected vertical line based on the image sensing clarity obtained in step S10040 for the selected vertical line. For example, the pixel value of each pixel of the line of the mask image corresponding to the selected vertical line is set to the image sensing clarity obtained in step S10040 for the selected vertical line.

In step S10060, the region detection unit 120 determines whether all vertical lines have been selected in step S4030. If an unselected vertical line exists upon determination, the process returns to step S4030. If all vertical lines have been selected, the process advances to step S10070.

In step S10070, the region detection unit 120 performs inverse conversion of equations (1) for the mask image. Note that when a linear probe is used as the image sensing unit of an ultrasonic image diagnosis apparatus 190, this step is unnecessary.

In step S10080, the region detection unit 120 outputs, to the image composition unit 140, the mask image representing the unclear image sensing region and its image sensing clarity obtained by the above-described processing. The above-described processing allows to detect the unclear image sensing region from the obtained tomographic image and calculate its image sensing clarity.

Figure 11:
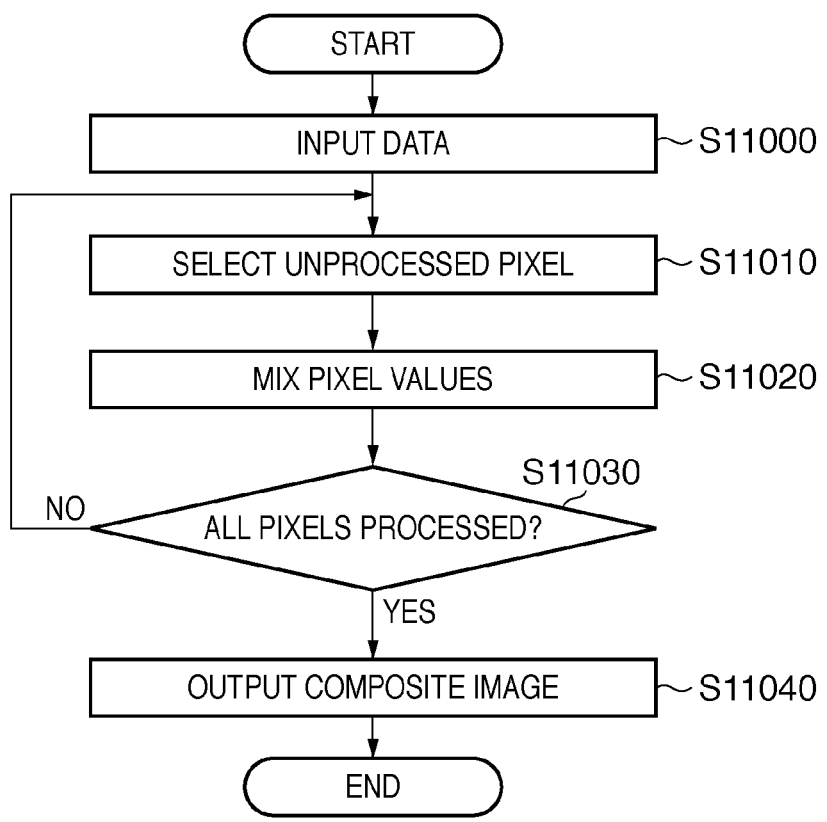
FIG. 11 is a flowchart of the process in step S3030 according to the fourth embodiment.

Processing to be executed by the image composition unit 140 of this embodiment in step S3030 will be described next with reference to FIG. 11. In step S11000, the image composition unit 140 receives the obtained tomographic image from a data input unit 110 and the mask image representing the unclear image sensing region and its image sensing clarity from the region detection unit 120. The image composition unit 140 also receives a generated tomographic image from an image generation unit 130.

In step S11010, the image composition unit 140 selects, as a selected pixel, an unselected pixel of the obtained tomographic image. In step S11020, the image composition unit 140 composes the pixel value of the selected pixel with the pixel value at the corresponding pixel position of the generated tomographic image based on the pixel value at a pixel position of the mask image corresponding to the selected pixel. For example, if the pixel value at the pixel position of the mask image corresponding to the selected pixel is $\alpha_1$, a pixel value $I_s$ of the selected pixel and a pixel value $I_g$ at the corresponding pixel position of the generated tomographic image are composed by $$I=(1-\alpha_1)I_s+\alpha_1 I_g \quad (3)$$

where I is the pixel value as the composition result of the pixel values $I_s$ and $I_g$. The image composition unit 140 replaces the pixel value $I_s$ of the selected pixel with the pixel value I obtained by the composition process. This composition process enables to compose the obtained tomographic image with the generated tomographic image at a composition ratio $\alpha_1$.

In step S11030, the image composition unit 140 determines whether all pixels in the obtained tomographic image have been selected in step S11010. If an unselected pixel exists upon determination, the process returns to step S11010. If all pixels in the obtained tomographic image have been selected, the process advances to step S11040.

In step S11040, the image composition unit 140 outputs the obtained tomographic image updated by the processing in steps S11000 to S11030 as the composite image of the obtained tomographic image and the generated tomographic image. The above-described processing enables to compose the unclear image sensing region in the obtained tomographic image with the generated tomographic image in accordance with the image sensing clarity.

As described above, according to this embodiment, it is possible to detect an unclear image sensing region in a tomographic image and compose it, in accordance with its image sensing clarity, with a tomographic image generated based on three-dimensional volume data. This allows to complement the unclear image sensing region based on the three-dimensional volume data without impeding observation of a clear image sensing region in the tomographic image. Note that in this embodiment, a case has been described in which a shadow region is handled as an unclear image sensing region. However, the unclear image sensing region is not limited to the shadow region and may be a posterior echo region.

Fifth Embodiment

In this embodiment, the image sensing clarities of regions of an obtained tomographic image are calculated using a plurality of methods corresponding to the properties of the unclear image sensing regions. In accordance with the image sensing clarities, the obtained tomographic image is composed with a generated tomographic image generated based on three-dimensional volume data. Note that in this embodiment, a case will be described in which a shadow region and a posterior echo region are handled as unclear image sensing regions, and three-dimensional volume data is handled as three-dimensional image data.

This embodiment will be described below regarding only portions different from the first embodiment. Note that the arrangement of an image processing apparatus according to this embodiment is the same as in FIG. 1 except only the functions of a region detection unit 120 and an image composition unit 140. In this embodiment, the region detection unit 120 calculates the image sensing clarity of a region in an obtained tomographic image.

Figure 12:
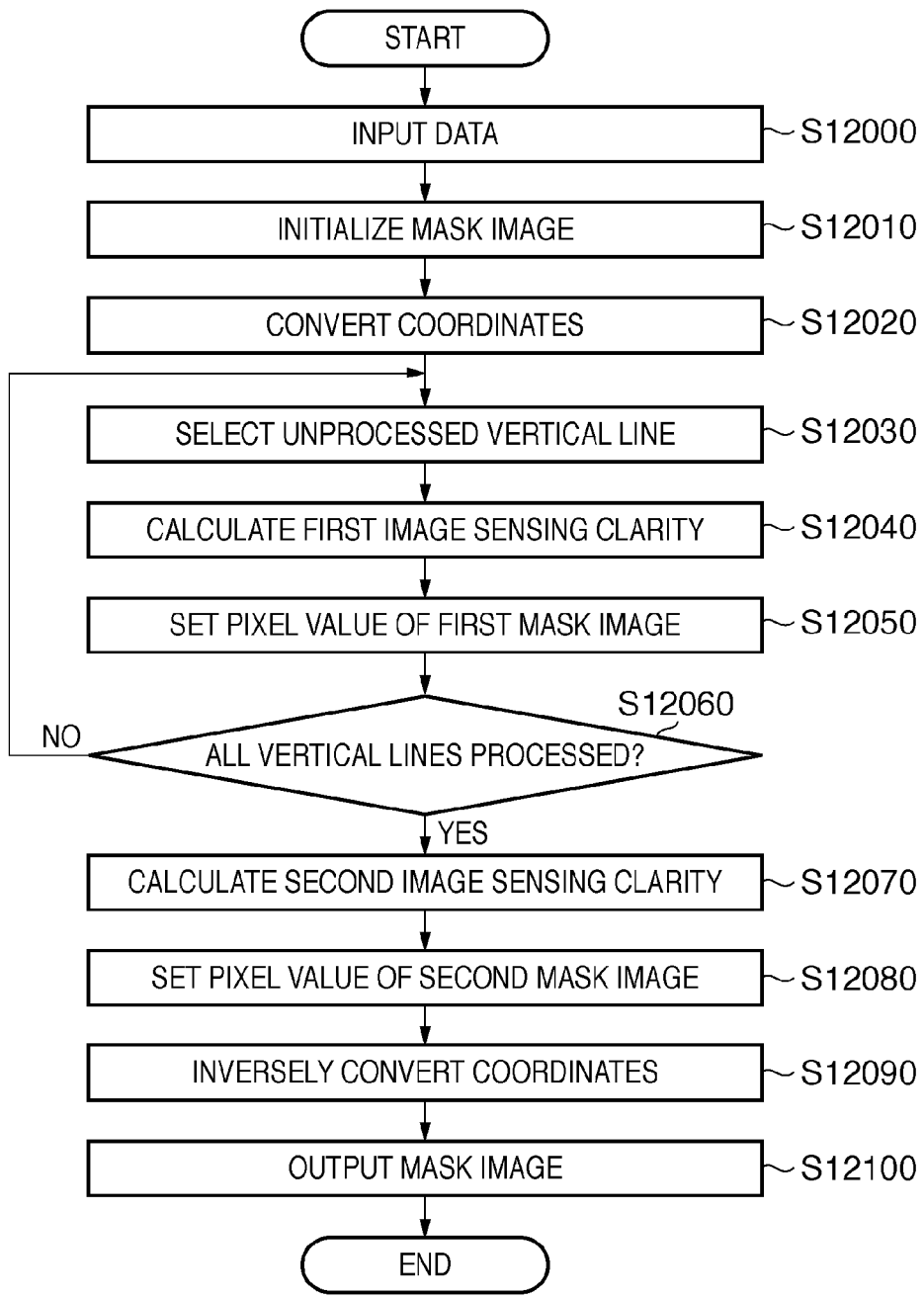
FIG. 12 is a flowchart of the process in step S3010 according to the fifth embodiment.

Processing to be executed by the region detection unit 120 of this embodiment in step S3010 will be described next with reference to FIG. 12. In step S12000, the region detection unit 120 acquires an obtained tomographic image from a data input unit 110. In step S12010, the region detection unit 120 generates two images each having the same size as that of the obtained tomographic image received in step S12000. One of the images will be referred to as a first mask image, and the other will be referred to as a second mask image. Note that the pixel values of all pixels of the mask images are set to 0.

In step S12020, the region detection unit 120 converts the image sensing region of the obtained tomographic image into a rectangle, and performs the same conversion for the first mask image and the second mask image. When a convex probe is used as the image sensing unit of the ultrasonic image diagnosis apparatus, the image sensing region is converted into a rectangle by, e.g., equations (1). When a linear probe is used as the image sensing unit of the ultrasonic image diagnosis apparatus, the image sensing region is rectangular, and this step is unnecessary.

In step S12030, the region detection unit 120 selects, as a selected vertical line, an unprocessed vertical line in the rectangle region of the obtained tomographic image. In step S12040, the region detection unit 120 calculates the shadow region likelihood (first image sensing clarity) of the selected vertical line as a value ranging from 0 to 1. For example, a first image sensing clarity $R_1$ is calculated by equation (2). For $R_1 < 0$, $R_1 = 0$ is set.

In step S12050, the region detection unit 120 sets the pixel value of each pixel of a line of the mask image corresponding to the selected vertical line based on the first image sensing clarity $R_1$ obtained in step S12040 for the selected vertical line. For example, the pixel value of each pixel of the line of the mask image corresponding to the selected vertical line is set to the first image sensing clarity $R_1$ obtained in step S12040 for the selected vertical line.

In step S12060, the region detection unit 120 determines whether all vertical lines have been selected in step S12030. If an unselected vertical line exists upon determination, the process returns to step S12030. If all vertical lines have been selected, the process advances to step S12070.

In step S12070, the region detection unit 120 detects a posterior echo region in the image sensing region of the obtained tomographic image. At this time, the region detection unit 120 calculates the posterior echo region likelihood (second image sensing clarity) as a value ranging from 0 to 1.

Figure 13:
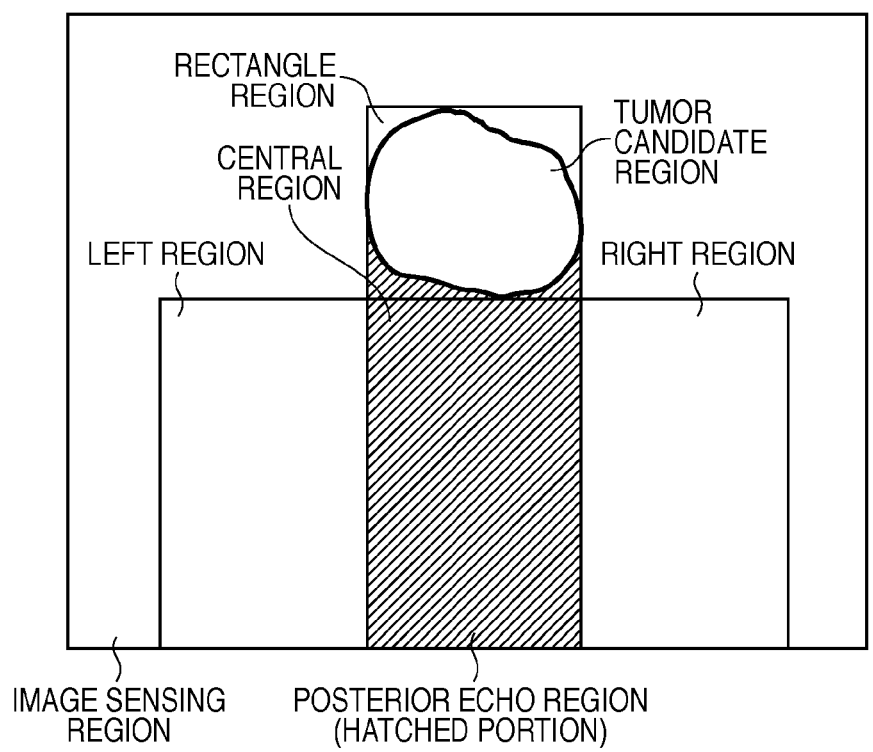
FIG. 13 is a view showing a central region, left region, and right region based on a posterior echo region.

For example, using a method based on vertical edge detection disclosed in reference 2, a tumor candidate region serving as a part region of interest is detected first from the image sensing region converted into a rectangle. Next, a rectangle region including the tumor candidate region is set. Three regions as shown in FIG. 13 are set behind (under) the rectangle region. A region that combines the central region (the region immediately under the tumor candidate region) and a rectangle region behind (under) the tumor candidate region is the posterior echo region. Based on the average luminance value of the left region and the right region (the average luminance value of regions adjacent to the left and right sides of the region immediately under the tumor candidate region) and the average luminance value of the central region, a second image sensing clarity $R_2$ is calculated by $$R_2 = \frac{I_{lr} - I_c}{I_{lr}} \quad (4)$$

(when $I_{lr} \geq I_c$)

$$R_2 = \frac{I_c - I_{lr}}{I_{max} - I_{lr}}$$

(when $I_{lr} < I_c$)

where $I_{lr}$ is the average luminance value of the left and right regions, $I_c$ is the average luminance value of the central region, and $I_{max}$ is the maximum value that the luminance value can take. That is, these equations obtain a value by dividing the difference between $I_c$ and $I_{lr}$ by $I_{lr}$ or the difference between $I_{max}$ and $I_{lr}$.

In step S12080, based on the second image sensing clarity $R_2$ calculated in step S12070, the region detection unit 120 sets the pixel value of each pixel of a region of the second mask image corresponding to the posterior echo region detected in step S12070. For example, the pixel value of each pixel of the region of the second mask image corresponding to the posterior echo region detected in step S12070 is set to the second image sensing clarity $R_2$ calculated in step S12070.

In step S12090, the region detection unit 120 performs inverse conversion of equations (1) for the first mask image and the second mask image. Note that when a linear probe is used as the image sensing unit of the ultrasonic image diagnosis apparatus, this step is unnecessary.

In step S12100, the region detection unit 120 outputs, to the image composition unit 140, the first mask image and the second mask image obtained by the processing in steps S12000 to S12090. The above-described processing allows to detect the unclear image sensing regions having different properties from the obtained tomographic image and calculate their image sensing clarities.

Figure 14:
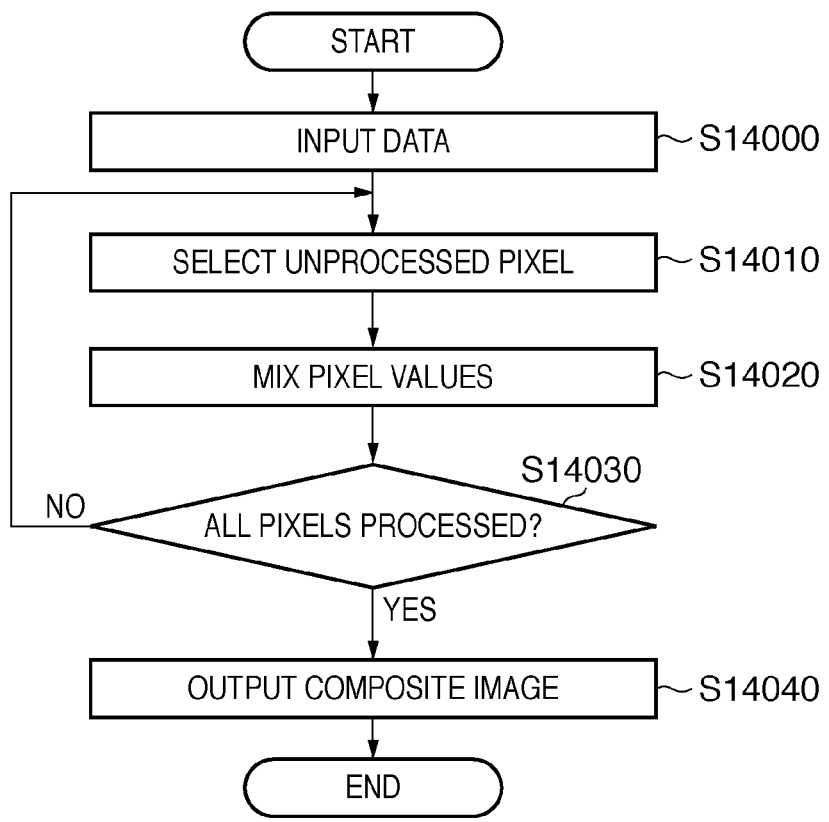
FIG. 14 is a flowchart of the process in step S3030 according to the fifth embodiment.

Processing to be executed by the image composition unit 140 of this embodiment in step S3030 will be described next with reference to FIG. 14. In step S14000, the image composition unit 140 receives the obtained tomographic image from the data input unit 110 and the first and second mask images representing the unclear image sensing regions and their image sensing clarities from the region detection unit 120. The image composition unit 140 also receives a generated tomographic image from an image generation unit 130.

In step S14010, the image composition unit 140 selects, as a selected pixel, one unselected pixel of the obtained tomographic image. In step S14020, the image composition unit 140 decides the pixel value of the selected pixel. More specifically, the image composition unit 140 composes the pixel value of the selected pixel with the pixel value at the corresponding pixel position of the generated tomographic image based on the pixel value $R_1$ at a pixel position of the first mask image corresponding to the selected pixel and the pixel value $R_2$ at a pixel position of the second mask image corresponding to the selected pixel.

For example, if $R_1=\alpha_1$, and $R_2=\alpha_2$, a pixel value $I_s$ of the selected pixel and a pixel value $I_g$ at the corresponding pixel position of the generated tomographic image are composed by $$I=(1-\alpha_1)(1-\alpha_2)I_s+(\alpha_1+\alpha_2-\alpha_1\alpha_2)I_g \quad (5)$$

where I is the pixel value as the composition result of the pixel values $I_s$ and $I_g$. The image composition unit 140 replaces the pixel value $I_s$ of the selected pixel with the pixel value I obtained by the composition process. This composition process enables to compose the obtained tomographic image with the generated tomographic image at composition ratios $\alpha_1$ and $\alpha_2$.

In step S14030, the image composition unit 140 determines whether all pixels in the obtained tomographic image have been selected in step S14010. If an unselected pixel exists upon determination, the process returns to step S14010. If all pixels in the obtained tomographic image have been selected, the process advances to step S14040.

In step S14040, the image composition unit 140 outputs the obtained tomographic image updated by the processing in steps S14000 to S14030 as the composite image of the obtained tomographic image and the generated tomographic image. The above-described processing enables to compose the unclear image sensing region in the obtained tomographic image with the generated tomographic image in accordance with the image sensing clarity.

As described above, according to this embodiment, it is possible to detect unclear image sensing regions in a tomographic image by a plurality of methods and compose them, in accordance with their image sensing clarities, with a tomographic image generated based on three-dimensional volume data. This allows to complement the unclear image sensing regions based on the three-dimensional volume data without impeding observation of a clear image sensing region in the tomographic image. Note that in this embodiment, a posterior echo region is detected after detection of a shadow region. However, the regions may be detected in a reversed order or in parallel.

Sixth Embodiment

In this embodiment, the image sensing clarity of a region of an obtained tomographic image is calculated using a method corresponding to the property of the unclear image sensing region. In addition, based on the three-dimensional reliability distribution of three-dimensional image data, the reliability distribution in a tomographic image generated based on the three-dimensional image data is calculated. An obtained tomographic image and a generated tomographic image are composed based on the image sensing clarity of the obtained tomographic image and the reliability distribution in the generated tomographic image. Note that in this embodiment, a case will be described in which a shadow region is handled as an unclear image sensing region, and three-dimensional volume data is handled as three-dimensional image data.

This embodiment will be described below regarding only portions different from the fourth embodiment. Note that the arrangement of an image processing apparatus according to this embodiment is the same as in FIG. 1 except only the functions of an image generation unit 130 and an image composition unit 140. In this embodiment, the image generation unit 130 calculates the reliability distribution in a generated tomographic image based on the three-dimensional reliability distribution of three-dimensional volume data.

Figure 15:
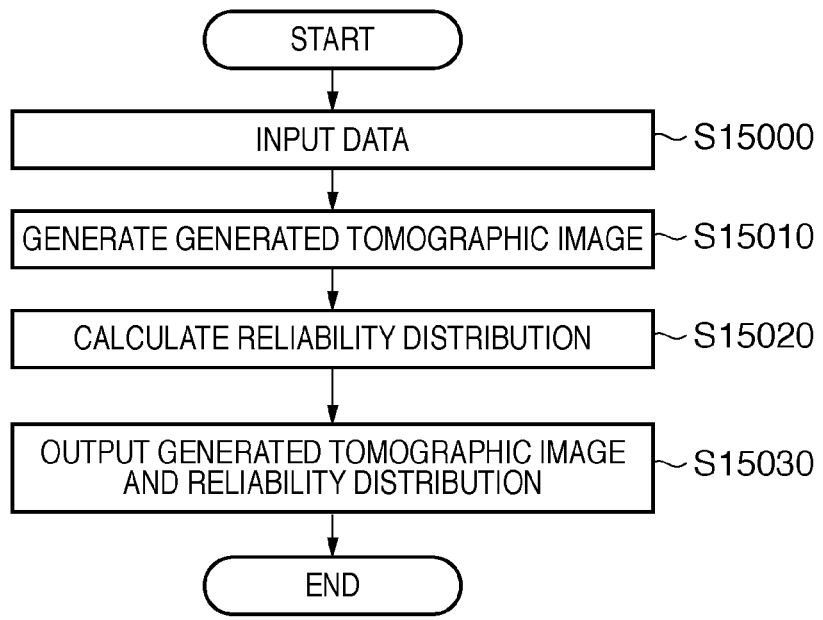
FIG. 15 is a flowchart of the process in step S3020 according to the sixth embodiment.

Processing to be executed by the image generation unit 130 of this embodiment in step S3020 will be described next with reference to FIG. 15.

In step S15000, the image generation unit 130 receives, from a data input unit 110, three-dimensional volume data, the three-dimensional reliability distribution of the three-dimensional volume data calculated in advance, and the position and orientation information of an obtained tomographic image on the reference coordinate system.

The three-dimensional volume data is reconstructed from a tomographic image group obtained by an ultrasonic image diagnosis apparatus 190. Hence, the reliability is not uniform between the voxels of the three-dimensional volume data. For example, a region where the tomographic images are obtained densely while slowly moving the ultrasonic probe has a high reliability. On the other hand, a region where the tomographic images are obtained coarsely while moving the ultrasonic probe at a high speed has a low reliability. For example, the number of tomographic images used upon reconstructing the voxel values of the three-dimensional volume data from the tomographic image group is divided by the maximum value of the number of used tomographic images, and the quotient is normalized within the range of 0 to 1. The resultant value is defined as a reliability $L_v$ of each voxel.

In step S15010, based on the position and orientation information acquired in step S15000, the image generation unit 130 generates a tomographic image by extracting, from the three-dimensional volume data, an image of the same slice as that of the obtained tomographic image acquired by the data input unit 110.

In step S15020, the image generation unit 130 calculates a reliability $L_p$ of each pixel of the generated tomographic image based on the reliability $L_v$ of each voxel used to generate the pixels of the generated tomographic image. For example, when the value of each pixel is set to the value of the nearest voxel, the reliability $L_p$ of a given pixel is set to the reliability $L_v$ of the nearest voxel.

In step S15030, the image generation unit 130 outputs, to the image composition unit 140, the generated tomographic image and the reliabilities (reliability distribution) of the pixels of the generated tomographic image. The above-described processing enables to calculate the generated tomographic image and the reliability distribution of it.

Figure 16:
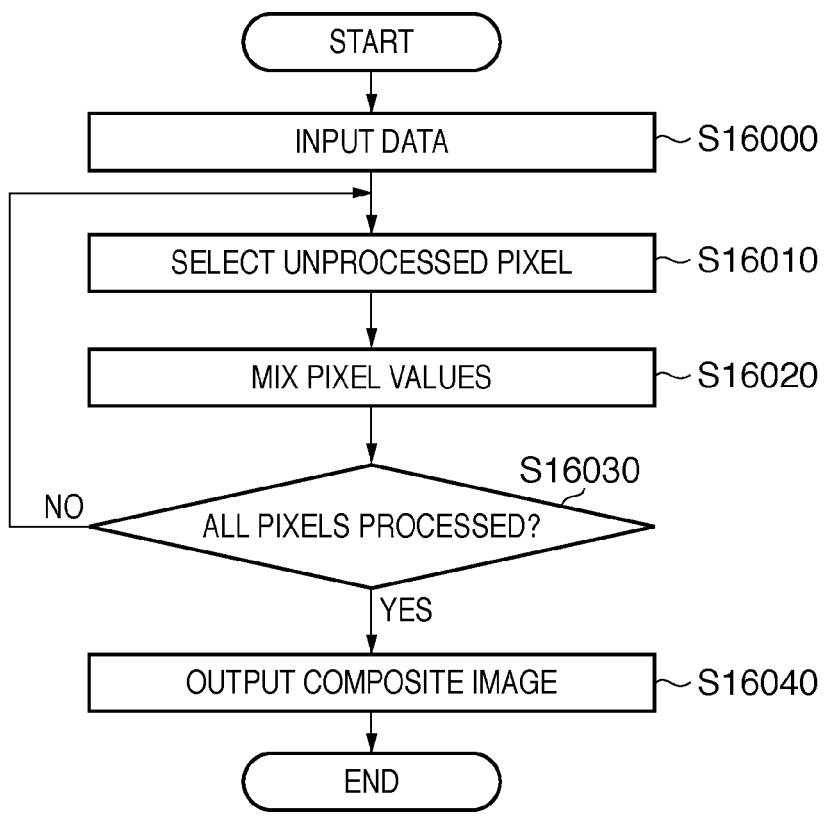
FIG. 16 is a flowchart of the process in step S3030 according to the sixth embodiment.
Figure 17:
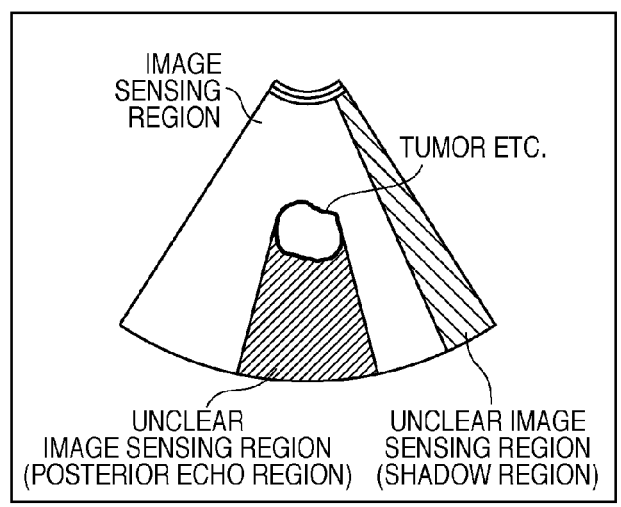
FIG. 17 is a view for explaining an unclear image sensing region.

Processing to be executed by the image composition unit 140 of this embodiment in step S3030 will be described next with reference to FIG. 16. In step S16000, the image composition unit 140 receives the obtained tomographic image from the data input unit 110 and a mask image representing an unclear image sensing region and its image sensing clarity from a region detection unit 120. The image composition unit 140 also receives the generated tomographic image and its reliability distribution from the image generation unit 130.

In step S16010, the image composition unit 140 selects, as a selected pixel, an unselected pixel of the obtained tomographic image. In step S16020, the image composition unit 140 composes the pixel value of the selected pixel with the pixel value at the corresponding pixel position of the generated tomographic image based on the reliability at a pixel position of the generated tomographic image corresponding to the selected pixel and the pixel value at a pixel position of the mask image corresponding to the selected pixel. For example, assume that the reliability at the pixel position of the generated tomographic image corresponding to the selected pixel is $L_p$, and the pixel value at the pixel position of the mask image corresponding to the selected pixel is $\alpha_1$. In this case, a pixel value $I_s$ of the selected pixel and a pixel value $I_g$ at the corresponding pixel position of the generated tomographic image are composed by $$I=(1-\alpha_1 L_p)I_s+\alpha_1 L_p I_g \tag{6}$$

where I is the pixel value as the composition result of the pixel values $I_s$ and $I_g$. The image composition unit 140 replaces the pixel value $I_s$ of the selected pixel with the pixel value I obtained by the composition process.

In step S16030, the image composition unit 140 determines whether all pixels in the obtained tomographic image have been selected in step S16010. If an unselected pixel exists upon determination, the process returns to step S16010. If all pixels in the obtained tomographic image have been selected, the process advances to step S16040.

In step S16040, the image composition unit 140 outputs the obtained tomographic image updated by the processing in steps S16000 to S16030 as the composite image of the obtained tomographic image and the generated tomographic image. The above-described processing enables to compose the obtained tomographic image with the generated tomographic image in accordance with the image sensing clarity of the unclear image sensing region of the obtained tomographic image and the reliability distribution of the generated tomographic image.

As described above, according to this embodiment, it is possible to compose an obtained tomographic image with a generated tomographic image in accordance with the image sensing clarity of an unclear image sensing region of the obtained tomographic image and the reliability distribution of the generated tomographic image. This allows to complement the unclear image sensing region based on the three-dimensional volume data without impeding observation of a clear image sensing region in the tomographic image. Note that in this embodiment, a case has been described in which a shadow region is handled as an unclear image sensing region. However, the unclear image sensing region is not limited to the shadow region and may be a posterior echo region.

Seventh Embodiment

First Modification

In the above embodiments, an example has been described in which the ultrasonic image diagnosis apparatus 190 is used as a medical image collection apparatus for obtaining a tomographic image. However, the medical image collection apparatus for obtaining a tomographic image is not limited to this. For example, the methods of the above-described embodiments are applicable even when a medical image collection apparatus capable of obtaining a tomographic image, such as a magnetic resonance imaging apparatus (MRI), X-ray computerized tomography apparatus (X-ray CT), or optical coherence tomography (OCT) is used.

Second Modification

In the above embodiments, an example has been described in which the ultrasonic image diagnosis apparatus 190 obtains a tomographic image. However, the data acquired by the medical image collection apparatus is not limited to this. For example, the methods of the above-described embodiments are applicable even when acquiring an MPR (Multi Planar Reformat) image using a three-dimensional ultrasonic probe. That is, the methods of the above-described embodiments are directly applied to each of a plurality of slices.

Third Modification

In the above embodiments, an example has been described in which sequenced luminance value data reconstructed in advance from a tomographic image group obtained by previously causing the ultrasonic image diagnosis apparatus 190 to sense the object is used as three-dimensional image data. However, the three-dimensional image data to be used is not limited to this. For example, three-dimensional volume data acquired using a three-dimensional ultrasonic probe may be used. Alternatively, sequenced luminance value data reconstructed in advance from a tomographic image group obtained by previously causing a magnetic resonance imaging apparatus (MRI), X-ray computerized tomography apparatus (X-ray CT), or optical coherence tomography (OCT) to sense the object may be used. The sequenced luminance value data may be converted into sequenced luminance value data like data obtained by an ultrasonic image diagnosis apparatus. Three-dimensional CG data such as a standard geometric model may be used.

Note that not the sequenced luminance value data reconstructed in advance from a tomographic image group obtained previously by image sensing but sequenced luminance value data reconstructed in real time from a tomographic image group obtained in real time by image sensing may be used. In this case, the latest obtained tomographic image may be excluded form the tomographic image group to be used to reconstruct the sequenced luminance value data.

The tomographic image group obtained in advance or in real time by image sensing may directly used as the three-dimensional image data without reconstructing sequenced luminance value data from it. In this case, the generated tomographic image having almost the same slice as that of the obtained tomographic image is directly generated using, for example, a method disclosed in the following reference.

R. W. Prager, A. H. Gee, and L. Berman, "Stradx: real-time acquisition and visualisation of freehand 3D ultrasound," Technical report CUED/F-INFENG/TR 319, Cambridge University Department of Engineering, April 1998.

Fourth Modification

In the above embodiments, a case has been described in which an unclear image sensing region is detected from the obtained tomographic image, and the detected region is complemented based on three-dimensional volume data. However, if the unclear image sensing region is known, the processing of detecting it is unnecessary. For example, when the piezoelectric element (oscillator) of the ultrasonic probe is partially broken, a specific region of the image sensing region is always unclear because of the luminance lower than usual, like a shadow region. In this case, the specific region is, e.g., manually designated in advance, and the same processing as that for the shadow region in the above-described embodiments is performed for the designated region. At this time, the image sensing clarity of the unclear image sensing region may be calculated in advance, and composition of the unclear image sensing region may be done based on the image sensing clarity.

Fifth Modification

In the above embodiments, a case has been described in which an unclear image sensing region in the obtained tomographic image is complemented based on three-dimensional volume data. However, even the clear image sensing region may be mixed with the pixel values of the generated tomographic image at a ratio not to impede observation of the region. For example, all the pixel values of a region of the mask image where the pixel values are 0.1 or less are replaced with 0.1. After that, the pixel values of the obtained tomographic image and those of the generated tomographic image are mixed based on equation (3) in step S11020 or equation (5) in step S14020. This makes it possible to grasp the overview of the generated tomographic image without impeding observation of the clear image sensing region.

Sixth Modification

In the first embodiment, the clear image sensing region and the unclear image sensing region may be displayed in different display attributes. For example, the clear image sensing region may be displayed in blue of 256 tones, and the unclear image sensing region may be displayed in red of 256 tones. Only the unclear image sensing region may be blink. The boundary line between the clear image sensing region and the unclear image sensing region may be drawn.

That is, any display form can be adopted to display the composite image as far as the unclear image sensing region and other regions are displayed discriminately. This makes it possible to grasp the clear image sensing region and the unclear image sensing region without any confusion.

Seventh Modification

In the third embodiment, the unclear image sensing regions may be displayed in different display attributes in accordance with their properties. For example, a shadow region may be displayed in red of 256 tones, and a posterior echo region may be displayed in green of 256 tones. That is, any display form can be adopted to display the unclear image sensing regions as far as the unclear image sensing regions of different types are displayed discriminately. At this time, the clear image sensing region may be displayed in blue of 256 tones.

The color mixing ratio may be changed in accordance with the image sensing clarity, i.e., the pixel value of the mask image. If the pixel value of the first mask image representing a shadow region is $\alpha_1$, and the pixel value of the second mask image representing a posterior echo region is $\alpha_2$, the mixing ratio B:R:G of blue, red, and green can be calculated by, e.g., $$B:R:G = (1-\alpha_1)(1-\alpha_2) : \frac{\alpha_1(\alpha_1 + \alpha_2 - \alpha_1\alpha_2)}{\alpha_1 + \alpha_2} : \frac{\alpha_2(\alpha_1 + \alpha_2 - \alpha_1\alpha_2)}{\alpha_1 + \alpha_2} \quad (7)$$

That is, any display form can be adopted to display the composite image as far as its pixel values are displayed in display forms according to values corresponding to the image sensing clarity and reliability. All or some of the above-described embodiments and modifications may be combined as needed.

Eighth Embodiment

An image processing apparatus according to this embodiment time-serially (continuously in terms of time) acquires tomographic images of an object from an ultrasonic image diagnosis apparatus, and reconstructs the three-dimensional shape data of the object based on the obtained tomographic image group. At this time, a tomographic image obtained immediately after the ultrasonic probe has been brought into contact with the object and a tomographic image obtained immediately before the contact is canceled (immediately before the noncontact) are processed using a method different from that for remaining tomographic images. This reduces the influence of deformation caused by the probe pressure.

The tomographic image obtained immediately after the contact need not always be a single tomographic image but may include a designated number of tomographic images. All tomographic images obtained after the contact until the probe moves by a predetermined distance and/or angle may be handled as the tomographic images immediately after the contact. Note that the movement of the probe can be measured by a position and orientation sensor to be described later. The tomographic image obtained immediately before the noncontact need not always be a single tomographic image, like the tomographic image immediately after the contact.

In this embodiment, volume data that stores a luminance value in each voxel of a three-dimensional voxel mesh (to be referred to as sequenced luminance value data hereinafter) is reconstructed as three-dimensional shape data. This embodiment will be explained below.

Figure 18:
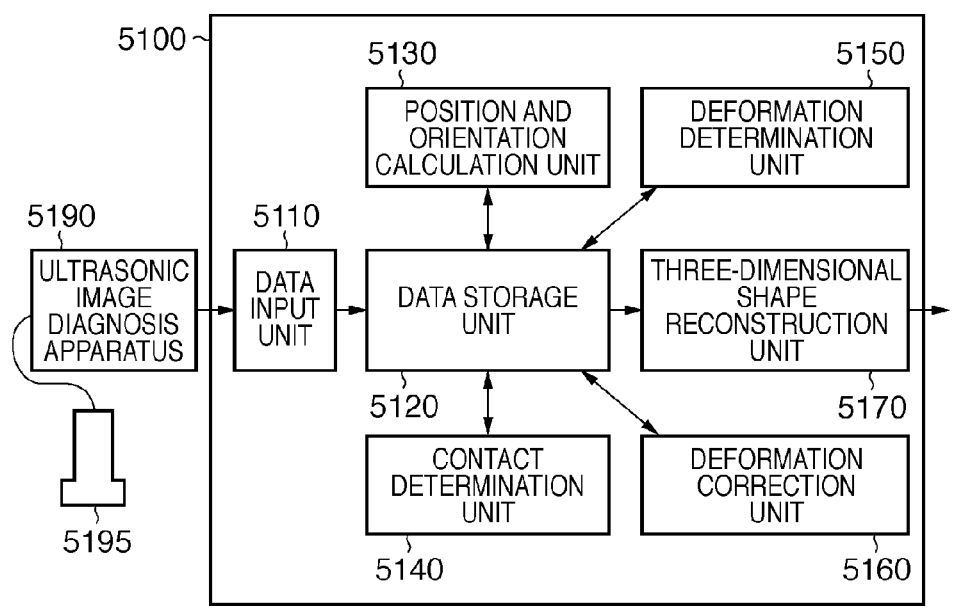
FIG. 18 is a block diagram showing an example of the functional arrangement of an image processing apparatus according to the eighth embodiment.

An example of the functional arrangement of the image processing apparatus according to this embodiment will be described first with reference to FIG. 18. As shown in FIG. 18, an image processing apparatus 5100 according to this embodiment includes a data input unit 5110, data storage unit 5120, position and orientation calculation unit 5130, contact determination unit 5140, deformation determination unit 5150, deformation correction unit 5160, and three-dimensional shape reconstruction unit 5170. An ultrasonic image diagnosis apparatus 5190 serving as a medical image collection apparatus for obtaining a tomographic image is connected to the image processing apparatus 5100.

The ultrasonic image diagnosis apparatus 5190 time-serially obtains tomographic images of an object. An ultrasonic probe 5195 configured to acquire a tomographic image group is connected to the ultrasonic image diagnosis apparatus 5190. Tomographic image sensing is done by bringing the ultrasonic probe 5195 into contact with the object. The tomographic image group obtained by the ultrasonic image diagnosis apparatus 5190 is input to the image processing apparatus 5100 via the data input unit 5110. A position and orientation sensor is attached to the ultrasonic probe 5195 to measure the position and orientation of the ultrasonic probe, as in the first embodiment. In this embodiment as well, any method capable of acquiring the position and orientation of the ultrasonic probe 5195 is usable. In all methods, the position and orientation information of the ultrasonic probe 5195 is input to the image processing apparatus 5100 via the data input unit 5110. The position and orientation information of the ultrasonic probe 5195 is expressed by a position and orientation on the above-described reference coordinate system. Note that the position and orientation of the ultrasonic probe 5195 may be input by the operator using a user interface such as a keyboard or mouse (not shown).

The data input unit 5110 time-serially receives, from the ultrasonic image diagnosis apparatus 5190, tomographic images and the position and orientation information of the ultrasonic probe 5195 at the point of time the tomographic images have been obtained. The data input unit 5110 converts each input tomographic image into digital data as needed, and stores the data in the data storage unit 5120 in association with the position and orientation information of the ultrasonic probe 5195 at the point of time the tomographic image has been obtained.

The position and orientation calculation unit 5130 reads out the position and orientation information of the ultrasonic probe 5195 from the data storage unit 5120. The position and orientation calculation unit 5130 also reads out the "position and orientation information of a tomographic image on an ultrasonic probe coordinate system", which is calculated in advance and managed in the data storage unit 5120. Using the position and orientation information, the position and orientation calculation unit 5130 calculates the position and orientation information of the tomographic image on the reference coordinate system, and stores it in the data storage unit 5120. The ultrasonic probe coordinate system is a coordinate system whose origin is defined at one point on the ultrasonic probe 5195, and whose X-, Y-, and Z-axes are defined as three axes that cross at right angles at that origin.

The contact determination unit 5140 reads out a tomographic image from the data storage unit 5120, and using the readout tomographic image, determines the presence/absence of contact between the ultrasonic probe 5195 and the object at the sensing time of the tomographic image. The contact determination unit 5140 stores information representing the determination result (presence/absence of contact) in the data storage unit 5120.

The deformation determination unit 5150 reads out, from the data storage unit 5120, a tomographic image and information representing the presence/absence of contact determined using the tomographic image. The deformation determination unit 5150 determines, using the readout tomographic image and information representing the presence/absence of contact, whether the tomographic image is a tomographic image (slightly deformed tomographic image) having slight deformation caused by the pressure of the ultrasonic probe 5195 or a tomographic image (deformed tomographic image) having large deformation. The deformation determination unit 5150 stores information representing the determination result in the data storage unit 5120.

The deformation correction unit 5160 reads out, from the data storage unit 5120, a tomographic image, the position and orientation information of the tomographic image on the reference coordinate system, and information representing the result of determination performed for the tomographic image by the deformation determination unit 5150. The deformation correction unit 5160 corrects deformation of the deformed tomographic image based on the pieces of readout information, and stores, in the data storage unit 5120, the tomographic image that has undergone the deformation correction. Note that the tomographic image that has undergone the deformation correction will be referred to as a corrected tomographic image hereinafter.

The three-dimensional shape reconstruction unit 5170 reads out, from the data storage unit 5120, a slightly deformed tomographic image group, a corrected tomographic image group, and their position and orientation information on the reference coordinate system. The three-dimensional shape reconstruction unit 5170 reconstructs sequenced luminance value data using the pieces of readout information, and outputs the data to an external device.

The data storage unit 5120 stores the following data.

(1) Time-serially acquired tomographic images of an object and information about them (1-1) Tomographic images of the object input from the data input unit 5110

(1-2) The position and orientation information of each tomographic image on the reference coordinate system, which is input from the position and orientation calculation unit 5130

(1-3) Information representing the presence/absence of contact input from the contact determination unit 5140

(1-4) Information representing the result of determination by the deformation determination unit 5150, which is input from the deformation determination unit 5150

(1-5) Corrected tomographic images input from the deformation correction unit 5160

(2) The position and orientation information of each tomographic image on the ultrasonic probe coordinate system, which is calculated in advance These data are input/output to/from the data storage unit 5120 as needed. Note that at least some of the data input unit 5110, data storage unit 5120, position and orientation calculation unit 5130, contact determination unit 5140, deformation determination unit 5150, deformation correction unit 5160, and three-dimensional shape reconstruction unit 5170 shown in FIG. 18 may be implemented as independent devices. Alternatively, the units may be implemented as software applications which are installed in one or a plurality of computers and executed by the CPUs of the computers to implement corresponding functions. In this embodiment, the units of the image processing apparatus 5100 are assumed to be implemented as software and installed in a single computer. As the computer, a computer having the configuration example shown in FIG. 2 is applied, as in the first embodiment.

Figure 19:
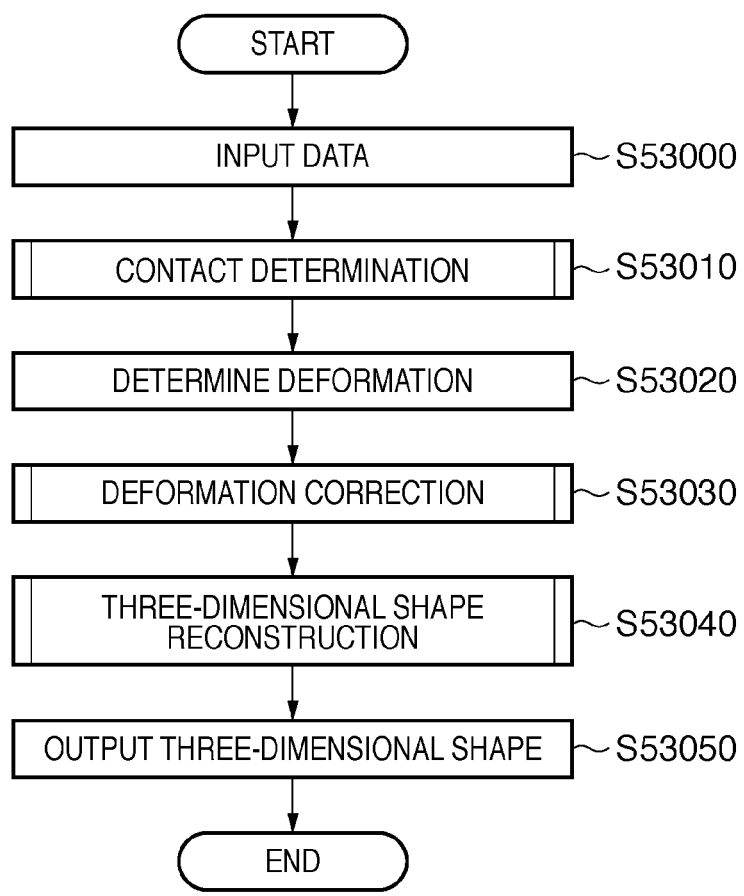
FIG. 19 is a flowchart illustrating the operation of the image processing apparatus according to the eighth embodiment.

Processing to be executed by the image processing apparatus 5100 according to the embodiment will be described next with reference to FIG. 19. Note that in the following explanation, the units shown in FIG. 18 are the entities of processing. In this embodiment, however, a CPU 1001 executes computer programs corresponding to the units, as described above. Hence, the CPU 1001 is the entity of processing in fact.

As described above, the ultrasonic image diagnosis apparatus 5190 sequentially outputs the tomographic images of the object, and the position and orientation information of the ultrasonic probe 5195 at the points of time the tomographic images have been obtained. Hence, in step S53000, the data input unit 5110 sequentially acquires the tomographic images of the object, and the position and orientation information of the ultrasonic probe 5195 at the points of time the tomographic images have been obtained, and stores the data in the data storage unit 5120.

Next, the position and orientation calculation unit 5130 reads out the position and orientation information of the ultrasonic probe 5195 from the data storage unit 5120. The position and orientation calculation unit 5130 also reads out the "position and orientation information of a tomographic image on the ultrasonic probe coordinate system", which is calculated in advance and stored in the data storage unit 5120. Using the pieces of position and orientation information, the position and orientation calculation unit 5130 calculates the position and orientation information of the tomographic image on the reference coordinate system, and stores it in the data storage unit 5120.

Figure 20:
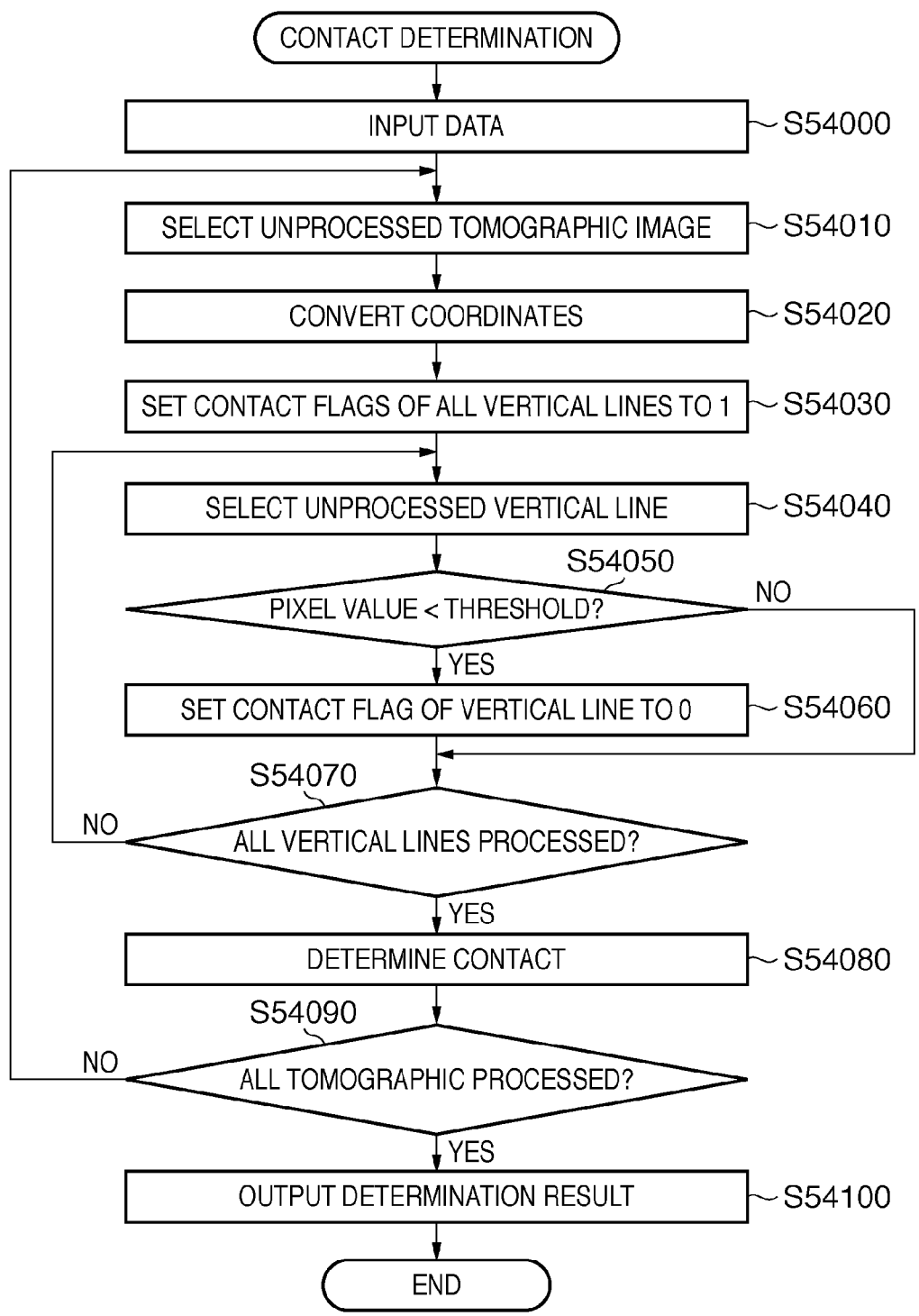
FIG. 20 is a flowchart of the process in step S53010 according to the eighth embodiment.

In step S53010, the contact determination unit 5140 determines the presence/absence of contact (contact or noncontact) between the ultrasonic probe 5195 and the object at the image sensing time of each tomographic image based on the tomographic image group stored in the data storage unit 5120 in step S53000. The contact determination unit 5140 stores, in the data storage unit 5120, information representing the presence/absence of contact at the image sensing time of each tomographic image. Note that the process in this step will be described later in detail with reference to the flowchart of FIG. 20.

In step S53020, for each of the tomographic images obtained in step S53000, the deformation determination unit 5150 determines, based on the contact determination result obtained in step S53010, whether the tomographic image is a slightly deformed tomographic image or a deformed tomographic image. More specifically, the deformation determination unit 5150 determines a tomographic image obtained immediately after the contact and that obtained immediately before cancel of the contact as slightly deformed tomographic images, and remaining tomographic images as deformed tomographic images. The deformation determination unit 5150 stores, in the data storage unit 5120, information representing the determination result of each tomographic image.

In step S53030, the deformation correction unit 5160 performs deformation correction processing for the tomographic images determined as deformed tomographic images in step S53020, thereby generating corrected tomographic images. The deformation correction unit 5160 stores the obtained corrected tomographic images in the data storage unit 5120. Note that the process in this step will be described later in detail with reference to the flowchart of FIG. 21.

In step S53040, the three-dimensional shape reconstruction unit 5170 reconstructs the sequenced luminance value data of the object using the tomographic image group (excluded from the correction target) determined as slightly deformed tomographic images in step S53020 and the corrected tomographic image group generated in step S53030. Note that the process in this step will be described later in detail with reference to the flowchart of FIG. 22.

In step S53050, the three-dimensional shape reconstruction unit 5170 outputs the sequenced luminance value data reconstructed in step S53040 to the outside via an I/F 1009. Alternatively, the sequenced luminance value data is stored in a RAM 1002 so as to be available for another application. The above-described processing allows to reconstruct three-dimensional shape data based on the acquired tomographic image group. The procedure of processing to be executed by the contact determination unit 5140 in step S53010 will be described next with reference to the flowchart shown in FIG. 20. In step S54000, the contact determination unit 5140 reads out the tomographic image group from the data storage unit 5120. In step S54010, the contact determination unit 5140 selects, as a selected tomographic image, an unselected tomographic image in the readout tomographic image group.

In step S54020, the contact determination unit 5140 converts the image sensing region of the selected tomographic image into a rectangle in accordance with equations (1). Note that when a linear probe is used as the ultrasonic probe 5195, the image sensing region is rectangular, and this step is unnecessary.

In step S54030, for all vertical lines in the rectangle region, the contact determination unit 5140 sets a flag representing the contact state to "1" that indicates contact. In step S54040, the contact determination unit 5140 selects, as a selected vertical line, an unselected vertical line in the rectangle region.

In step S54050, the contact determination unit 5140 determines whether the pixel values of all pixels of the selected vertical line are smaller than a threshold. The luminance is not necessarily low near the upper end portion of the image sensing region even if the ultrasonic probe 5195 is not in appropriate contact with the object surface. Not to use the upper end portion of the image sensing region, it may be determined whether the pixel values of all pixels at y-coordinates larger than a predetermined y-coordinate value are smaller than the threshold. If all the pixel values are smaller than the threshold upon determination, the process advances to step S54060. Otherwise, the process advances to step S54070.

Note that the processing of determining whether the pixel values of all pixels of the selected vertical line are smaller than the threshold is not limited to the above-described processing. For example, the determination may be done by checking whether the average of the pixel values of all pixels of the selected vertical line are equal to or smaller than a threshold, and the variance of the pixel values is equal to or smaller than a threshold.

In step S54060, the contact determination unit 5140 sets the flag representing the contact state of the selected vertical line to "0" that indicates noncontact, and advances the process to step S54070. In step S54070, the contact determination unit 5140 determines whether all vertical lines have been selected in step S54040. If an unselected vertical line remains in the selected tomographic image upon determination, the process returns to step S54040. If all vertical lines have been selected in the selected tomographic image, the process advances to step S54080.

In step S54080, the contact determination unit 5140 determines whether the flags (flag values) representing the contact states of all vertical lines are 0. If the flags representing the contact states of all vertical lines are 0 upon determination, the contact determination unit 5140 determines that the ultrasonic probe 5195 and the object are not in contact. Otherwise, it is determined that the ultrasonic probe and the object are in contact.

In step S54090, the contact determination unit 5140 determines whether a tomographic image yet to be selected in step S54010 exists. If an unselected tomographic image remains upon determination, the process returns to step S54010. If all tomographic images read out from the data storage unit 5120 in step S54000 have been selected in step S54010, the process advances to step S54100.

In step S54100, the contact determination unit 5140 stores, in the data storage unit 5120, information representing the result of determination performed for each tomographic image in step S54080. The above-described processing enables to determine whether the ultrasonic probe 5195 and the object are in contact at the image sensing time of each tomographic image.

Figure 21:
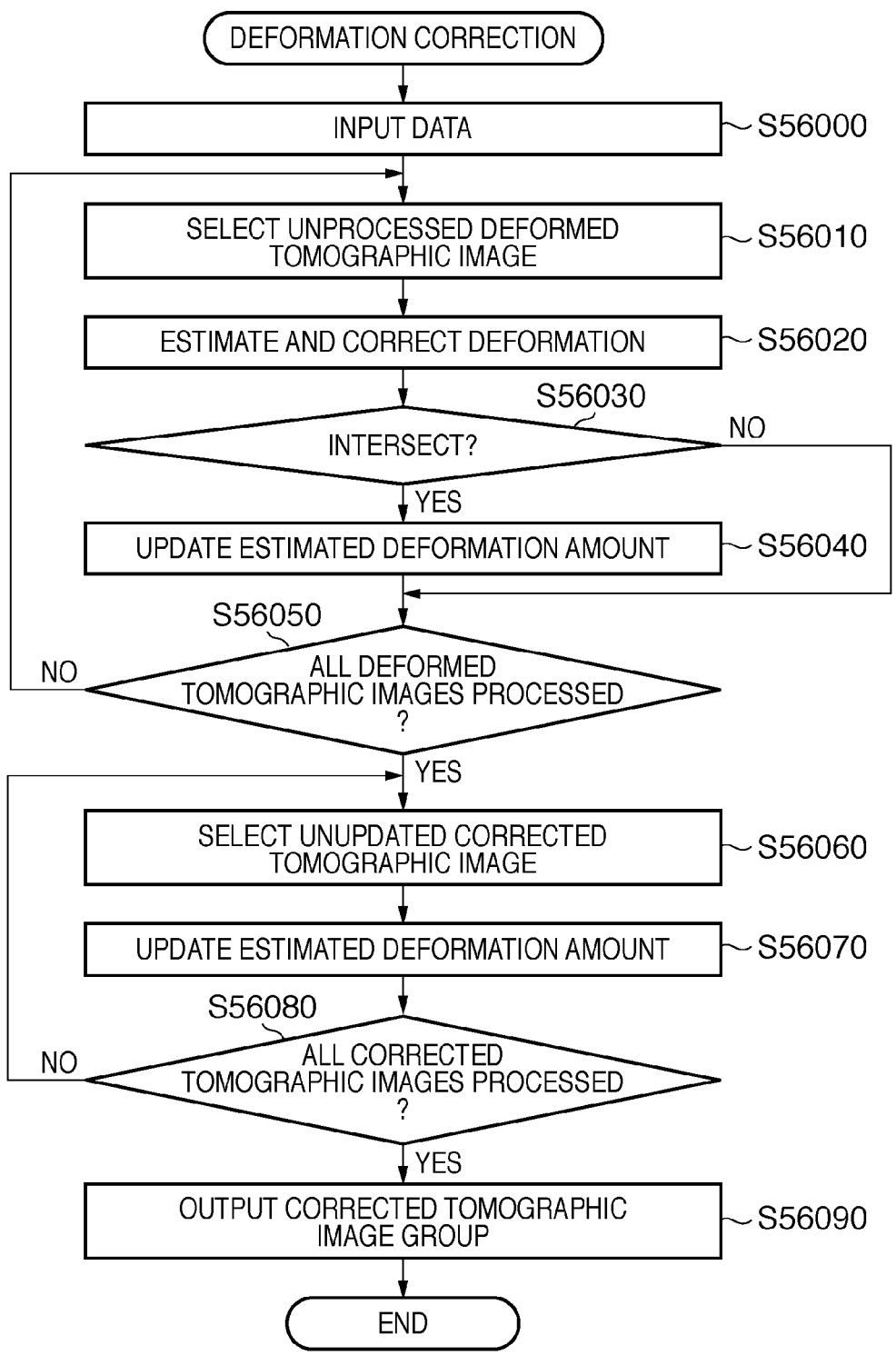
FIG. 21 is a flowchart of the process in step S53030 according to the eighth embodiment.

The procedure of processing to be executed by the deformation correction unit 5160 in step S53030 will be described next with reference to the flowchart shown in FIG. 21. In step S56000, the deformation correction unit 5160 receives, from the data storage unit 5120, the tomographic images, the position and orientation information of each tomographic image on the reference coordinate system, and information representing the result of determination performed for each tomographic image by the deformation determination unit 5150.

In step S56010, the deformation correction unit 5160 specifies deformed tomographic images out of the tomographic image group by referring the information representing the result of determination performed for each tomographic image by the deformation determination unit 5150. The deformation correction unit 5160 selects, as a selected deformed tomographic image, an unselected deformed tomographic image out of the specified deformed tomographic image group.

In step S56020, the deformation correction unit 5160 estimates a deformation amount d(y) of the selected deformed tomographic image corresponding to a depth y from the body surface using, e.g., the method disclosed in non-patent reference 5. The deformation correction unit 5160 generates a corrected tomographic image by correcting the deformation based on the estimation result.

Note that the processing of generating the corrected tomographic image is not limited to the above-described processing. For example, assuming that the deformation caused by the pressure of the ultrasonic probe 5195 is simple rigid conversion (translation), the deformation amount as a scalar value may be estimated and corrected. Alternatively, a deformation model may be created using, as a parameter, the amount of body surface push by the pressure of the ultrasonic probe 5195 so that the push amount is estimated assuming that, for example, the body surface is smooth, and the deformation is corrected based on the deformation model. With the process of this step, the initial value of the deformation amount d(y) is estimated, and a corrected tomographic image which has undergone rough deformation correction is generated.

In step S56030, the deformation correction unit 5160 determines intersection between the slightly deformed tomographic image group and the corrected tomographic image which has undergone the rough deformation correction processing in step S56020. To determine the intersection, a method of searching for the line of intersection by comparing the pixel values of two images, as disclosed in, e.g., the following reference, is used.

R. F. Chang, W-J. Wu, D-R. Chen, W-M Chen, W. Shu, J-H. Lee, and L-B. Jeng, "3-D US frame positioning using speckle decorrelation and image registration," Ultrasound in Med. & Biol., Vol. 29, No. 6, pp. 801-812, 2003.

If it is determined that the corrected tomographic image intersects one of the slightly deformed tomographic images, the process advances to step S56040. Otherwise, the process advances to step S56050. In step S56040, the deformation correction unit 5160 updates the estimated deformation amount d(y) of the corrected tomographic image by referring to the slightly deformed tomographic image that intersects the corrected tomographic image. More specifically, the deformation correction unit 5160 updates the estimated deformation amount d(y) of the corrected tomographic image by repeat calculation so as to maximize the similarity of pixel values on the line of intersection of the two images. For example, a deformation amount candidate group is generated by multiplying the estimated deformation amount d(y) of the corrected tomographic image by several kinds of coefficients close to 1.0. A candidate that maximizes the similarity is selected from the candidate group, thereby updating the estimated deformation amount. A corrected tomographic image is generated again using the obtained estimated deformation amount. An updated flag is added to the generated corrected tomographic image. The generated corrected tomographic image will be referred to as an updated corrected tomographic image hereinafter.

In step S56050, the deformation correction unit 5160 determines whether all deformed tomographic images have been selected in step S56010. If an unselected deformed tomographic image exists upon determination, the process returns to step S56010. If all deformed tomographic images have been selected, the process advances to step S56060.

In step S56060, the deformation correction unit 5160 selects a corrected tomographic image without an updated flag. That is, the deformation correction unit 5160 selects a corrected tomographic image which does not intersect any of the slightly deformed tomographic images and whose estimated deformation amount has not been updated yet.

In step S56070, the deformation correction unit 5160 updates the estimated deformation amount of the selected corrected tomographic image based on the estimated deformation amount of the updated corrected tomographic image. For example, let t be the image sensing time of the selected corrected tomographic image, $t_1$ be the image sensing time of an updated corrected tomographic image obtained at the nearest time before t, and $d_1(y)$ be the estimated deformation amount of the updated corrected tomographic image. Also let $t_2$ be the image sensing time of an updated corrected tomographic image obtained at the nearest time after t, and $d_2(y)$ be the estimated deformation amount of the updated corrected tomographic image. A new estimated deformation amount d'(y) of the selected corrected tomographic image is calculated by $$d'(y) = \frac{(t_2 - t)d_1(y) + (t - t_1)d_2(y)}{t_2 - t_1} \quad (8)$$

Note that the estimated deformation amount updating is not limited to the above-described method. For example, the new estimated deformation amount may be calculated by, e.g., obtaining the average of the estimated deformation amount d(y) before updating of the selected corrected tomographic image and the estimated deformation amount d'(y).

In step S56080, the deformation correction unit 5160 determines whether all corrected tomographic images without an updated flag have been processed. If the processing has not ended yet, the process returns to step S56060. If the processing has ended, the process advances to step S56090.

In step S56090, the deformation correction unit 5160 stores, in the data storage unit 5120, the corrected tomographic image group obtained by the processing in steps S56000 to S56080.

The above-described processing enables to effectively correct the deformation of the deformed tomographic image group based on the slightly deformed tomographic image group having slight deformation. That is, using the slightly deformed tomographic image group as a reference without deformation correction allows to obtain a corrected tomographic image group with less influence of deformation than in correcting deformation of all tomographic images without using a reference.

Figure 22:
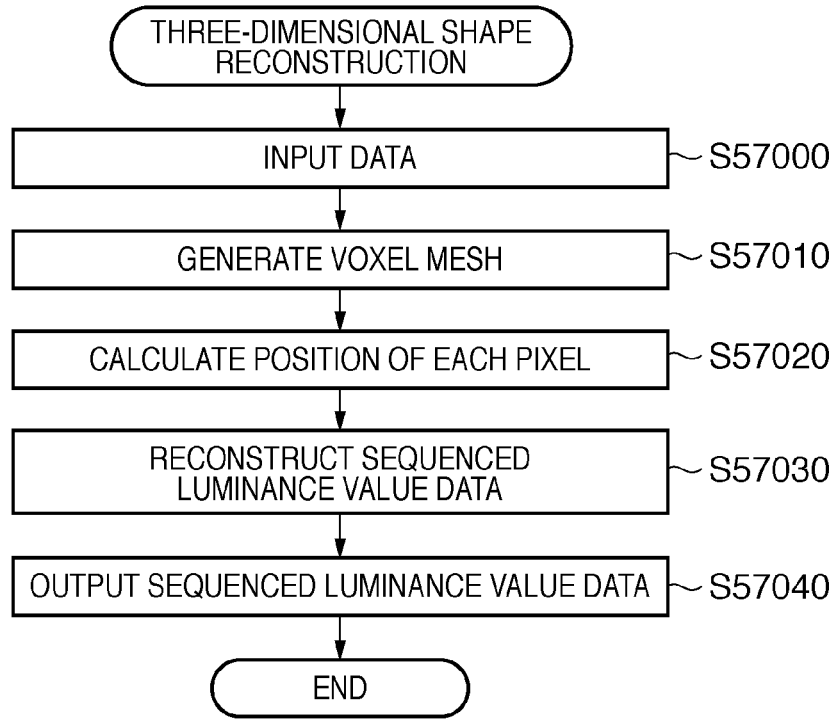
FIG. 22 is a flowchart of the process in step S53040 according to the eighth embodiment.

The procedure of processing to be executed by the three-dimensional shape reconstruction unit 5170 in step S53040 will be described next with reference to the flowchart shown in FIG. 22. In step S57000, the three-dimensional shape reconstruction unit 5170 reads out, from the data storage unit 5120, a slightly deformed tomographic image group, a corrected tomographic image group, and their position and orientation information on the reference coordinate system.

In step S57010, the three-dimensional shape reconstruction unit 5170 generates a voxel mesh formed from, e.g., 256×256×256 voxels to store sequenced luminance value data. The size of the voxel mesh is set so as to store all tomographic images inside. For a voxel mesh coordinate system, for example, the origin is defined at the central position of a given tomographic image, and three axes that cross at right angles at that origin are defined to coincide with those of the reference coordinate system.

In step S57020, the three-dimensional shape reconstruction unit 5170 calculates the position of each pixel of each tomographic image on the voxel mesh coordinate system based on the position and orientation information of each tomographic image on the reference coordinate system.

In step S57030, the three-dimensional shape reconstruction unit 5170 reconstructs sequenced luminance value data, i.e., calculates the luminance values of all voxels. The luminance value of each voxel is calculated by, for example, obtaining the weighted average of the luminance values of a plurality of pixels located near the voxel of interest by using the reciprocal of the distance from the voxel to each pixel as a weight.

In step S57040, the three-dimensional shape reconstruction unit 5170 outputs the sequenced luminance value data obtained in step S57030 to the outside via the I/F 1009. Alternatively, the sequenced luminance value data is stored in the RAM 1002 so as to be available for another application. The above-described processing allows to reconstruct the sequenced luminance value data as three-dimensional shape data with slight distortion based on the tomographic image group that has undergone deformation correction.

As described above, according to this embodiment, it is possible to reconstruct three-dimensional shape data with slight distortion based on a tomographic image group by processing tomographic images immediately after the ultrasonic probe 5195 has come into contact with the object and immediately before noncontact and remaining tomographic images by different methods. More specifically, in this embodiment, a slightly deformed tomographic image group which has a slight deformation caused by the pressure of the ultrasonic probe 5195 is used as a reference without correction. It is therefore possible to reconstruct three-dimensional shape data with less influence of deformation caused by the pressure of the ultrasonic probe 5195 than in correcting deformation of the tomographic image group without using a reference.

Ninth Embodiment

In the eighth embodiment, the volume data (sequenced luminance value data) of the object is reconstructed as three-dimensional shape data. In the ninth embodiment, the surface model (surface geometric model) of an object is reconstructed as three-dimensional shape data. This embodiment will be described below regarding only portions different from the eighth embodiment.

Figure 23:
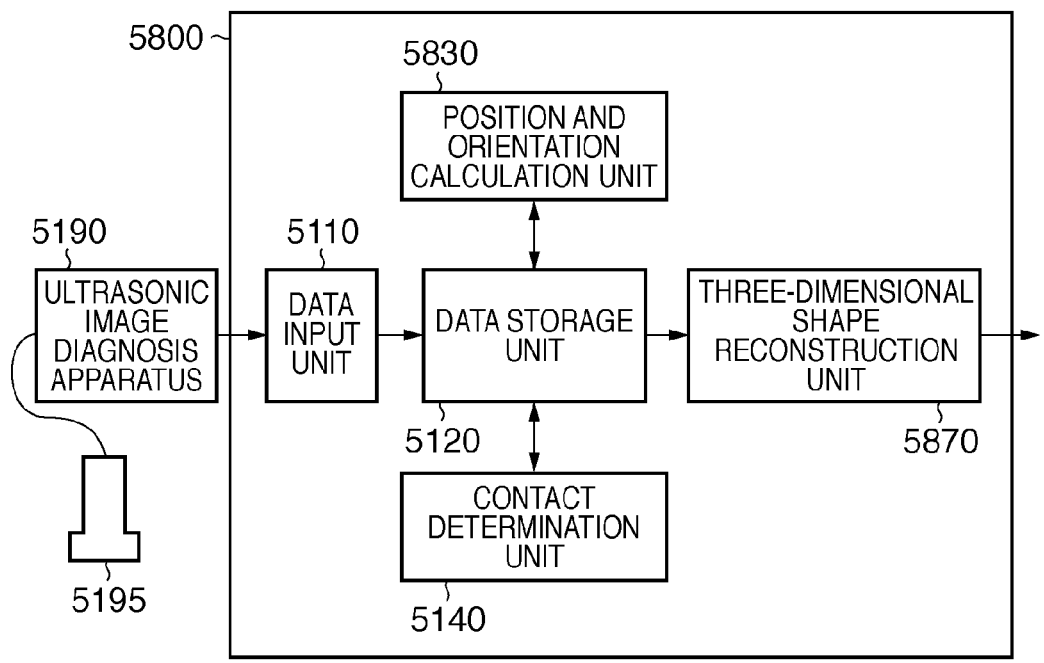
FIG. 23 is a block diagram showing an example of the functional arrangement of an image processing apparatus according to the ninth embodiment.

The functional arrangement of an image processing apparatus 5800 according to this embodiment will be described with reference to FIG. 23. Note that the same reference numerals as in FIG. 18 denote the same parts in FIG. 23, and a description thereof will not be repeated.

Figure 24:
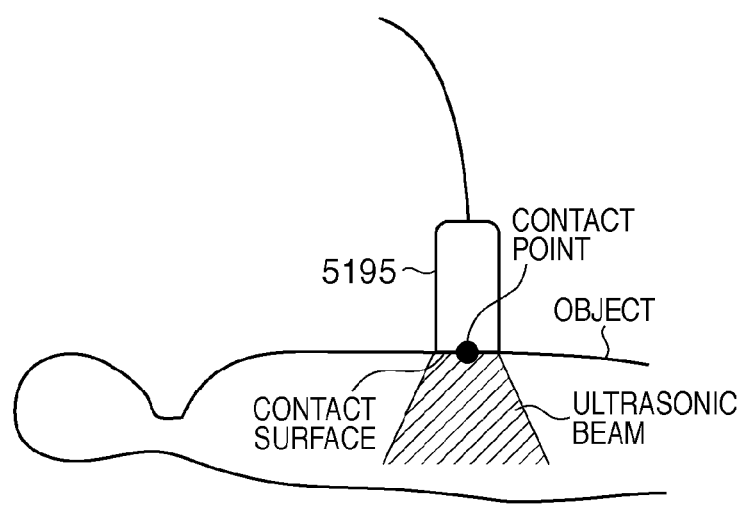
FIG. 24 is a view showing a state in which an object and an ultrasonic probe 5195 are in contact with each other.

A position and orientation calculation unit 5830 reads out, from a data storage unit 5120, the position and orientation of an ultrasonic probe 5195 on the reference coordinate system and the position information, which is calculated and stored in advance, of the contact point of the ultrasonic probe 5195 on the ultrasonic probe coordinate system. In this embodiment, the barycenter position of the contact surface between the object and the ultrasonic probe 5195 is defined as the contact point, as shown in FIG. 24. The position and orientation calculation unit 5830 calculates the contact point position information on the reference coordinate system based on the pieces of readout information, and stores the calculated position information in the data storage unit 5120.

Figure 25:
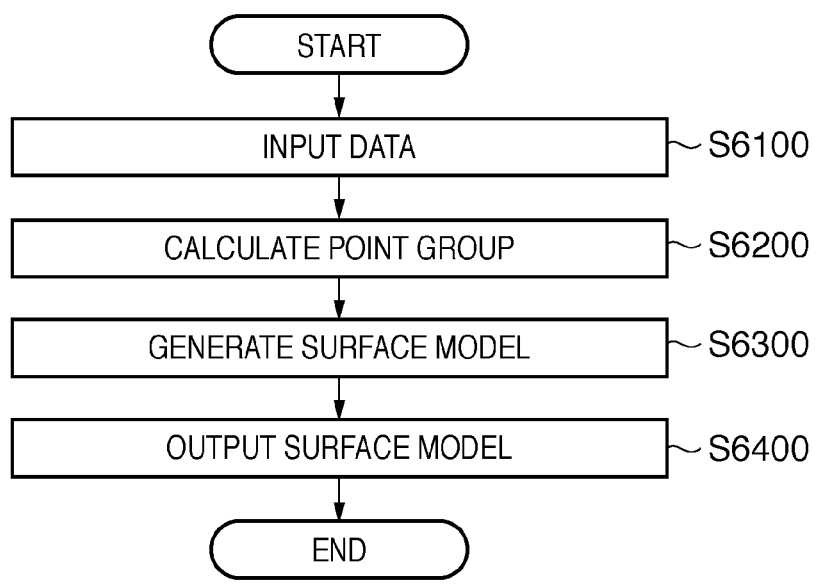
FIG. 25 is a flowchart illustrating the process in step S53040 according to the ninth embodiment.

Processing to be executed by a three-dimensional shape reconstruction unit 5870 in step S53040 will be described next with reference to the flowchart shown in FIG. 25. In step S6100, the three-dimensional shape reconstruction unit 5870 reads out, from the data storage unit 5120, contact point position information at the image sensing time of each tomographic image and information representing the determination result of contact between the ultrasonic probe 5195 and the object for each tomographic image.

In step S6200, the three-dimensional shape reconstruction unit 5870 obtains a point group representing the object surface based on the contact point position information at a point of time the contact determination result switches. More specifically, the positions of contact points immediately before and immediately after contact are averaged, thereby calculating the contact point position at the instant of contact. Similarly, the positions of contact points immediately before and immediately after noncontact are averaged, thereby calculating the contact point position at the instant of noncontact. These contact point groups form a point group representing the object surface.

In step S6300, the three-dimensional shape reconstruction unit 5870 reconstructs the surface model based on the point group representing the object surface. For example, triangle patches each having vertices corresponding to the points representing the object surface are generated so that a set of patches forms a surface model.

In step S6400, the three-dimensional shape reconstruction unit 5870 outputs the surface model obtained in step S6300 to the outside via an I/F 1009. Alternatively, the surface model is stored in a RAM 1002 so as to be available for another application. The above-described processing allows to reconstruct the surface model as three-dimensional shape data with slight distortion based on the determination result of contact between the ultrasonic probe 5195 and the object.

As described above, according to this embodiment, it is possible to reconstruct three-dimensional shape data with slight distortion based on the position and orientation of the ultrasonic probe 5195 at the timing the determination result of contact between the ultrasonic probe 5195 and the object switches. More specifically, this embodiment uses only the position and orientation when the object is deformed slightly by the pressure of the ultrasonic probe 5195. It is therefore possible to reconstruct three-dimensional shape data with less influence of deformation caused by the pressure of the ultrasonic probe 5195 than in using all positions and orientations.

Tenth Embodiment

An image processing apparatus according to this embodiment processes tomographic images obtained when the contact pressure between the ultrasonic probe and an object is weak using a method different from that for remaining tomographic images, thereby reconstructing three-dimensional shape data with slight distortion based on the tomographic image group. In this embodiment, a pressure sensor 5200 is attached to an ultrasonic probe 5195 to measure the contact pressure between the ultrasonic probe 5195 and an object. In this embodiment, sequenced luminance value data is reconstructed as three-dimensional shape data. This embodiment will be described below regarding only portions different from the eighth embodiment.

The functional arrangement of an image processing apparatus 5900 according to this embodiment will be described with reference to FIG. 26. Note that the same reference numerals as in FIG. 18 denote the same parts in FIG. 26, and a description thereof will not be repeated.

A data input unit 51110 acquires a tomographic image obtained by the ultrasonic probe 5195 and stores it in a data storage unit 5120, as in the eighth embodiment. The data input unit 51110 also stores, in the data storage unit 5120, a pressure value measured by the pressure sensor 5200 at the point of time the tomographic image has been obtained.

A deformation determination unit 51150 reads out, from the data storage unit 5120, the pressure values as the measured values of the pressure sensor 5200 and determines, using the readout pressure values, whether each tomographic image is a slightly deformed tomographic image or a deformed tomographic image. More specifically, when the pressure value of the pressure sensor 5200 is smaller than a threshold, the tomographic image obtained at the point of time the pressure value has been measured is determined as a slightly deformed tomographic image. When the pressure value is equal to or larger than the threshold, the tomographic image obtained at the point of time the pressure value has been measured is determined as a deformed tomographic image. The determination result is stored in the data storage unit 5120, as in the eighth embodiment.

As described above, according to this embodiment, it is possible to reconstruct three-dimensional shape data with slight distortion based on a tomographic image group by processing tomographic images obtained when the contact pressure between the ultrasonic probe 5195 and the object is small and remaining tomographic images by different methods.

Other Embodiments

First Modification

In the eighth and subsequent embodiments, an example has been described in which the ultrasonic image diagnosis apparatus 5190 acquires a two-dimensional tomographic image. However, the data acquired by the medical image collection apparatus is not limited to this. For example, a 2D array ultrasonic probe capable of acquiring a three-dimensional tomographic image may be used. In this case, the contact determination unit 5140 can perform determination processing by easily extending the processing for a two-dimensional tomographic image (flowchart in FIG. 20). The methods described in the eighth and subsequent embodiments are applicable even to a tomographic image group acquired in the range automatically scanned by the probe head.

Second Modification

In the eighth embodiment, a case has been described in which pieces of information immediately after contact between the ultrasonic probe 5195 and the object and immediately before noncontact are processed using a method different from that for other information, thereby reconstructing three-dimensional shape data with slight distortion based on a tomographic image group. However, if there are sufficient information immediately after contact between the ultrasonic probe 5195 and the object and immediately before noncontact, other information need not be used. In this case, correction of deformed tomographic images is unnecessary. Sequenced luminance value data is reconstructed based on a slightly deformed tomographic image group and their positions and orientations on the reference coordinate system.

Third Modification

In the eighth and ninth embodiments, if the flags representing the contact states of all vertical lines are 0 in the image sensing region of a tomographic image, it is determined that the ultrasonic probe 5195 and the object are not in contact. Otherwise, they are determined to be in contact. That is, whether or not an entire tomographic image is in the noncontact state is determined. However, the contact determination method is not limited to this. The noncontact state may be determined in each partial region of a tomographic image. For example, a partial region 2701 out of an image sensing region 2703 shown in FIG. 27 can be determined as a noncontact region, and the remaining partial regions can be determined as contact regions.

The contact region near the noncontact region is supposed to be deformed slightly by the probe pressure. The deformation correction unit 5160 can use such a partial region (to be referred to as a slightly deformed partial region) 2702 for deformation correction processing together with slightly deformed tomographic images. The deformation correction unit 5160 can improve the accuracy of deformation correction by using the slightly deformed tomographic images together.

Fourth Modification

In the eighth and ninth embodiments, contact between the ultrasonic probe 5195 and the object is determined based on tomographic images. However, the contact determination method is not limited to this. The determination may be done based on a contact sensor attached to the ultrasonic probe 5195 or the object. Use of the contact sensor obviates the contact determination unit 5140.

Fifth Modification

In the eighth and ninth embodiments, contact between the ultrasonic probe 5195 and the object is determined based on tomographic images. However, the contact determination method is not limited to this. The determination may be done based on the measured value of a position and orientation sensor. If the shape information of the object is known in advance, whether the ultrasonic probe 5195 and the object is in contact can easily be determined based on the measured value of the position and orientation sensor and the shape information of the object.

Sixth Modification

In the eighth embodiment, a method of measuring the position and orientation of the ultrasonic probe 5195 using a position and orientation sensor to obtain the positional relationship between tomographic images, thereby reconstructing three-dimensional shape data has been explained. However, the method of calculating the positional relationship between tomographic images is not limited to this. Calculation may be done without using the position and orientation sensor. For example, the method disclosed in non-patent reference 3 may be used to estimate the positional relationship between tomographic images based on the correlation between the image features in the tomographic images, thereby reconstructing three-dimensional shape data.

Seventh Modification

In the 10th embodiment, a case has been described in which pieces of information obtained when the contact pressure between the ultrasonic probe 5195 and the object is weak are processed using a method different from that for other information, thereby reconstructing three-dimensional shape data with slight distortion based on a tomographic image group. However, if there are sufficient pieces of information obtained when the contact pressure between the ultrasonic probe 5195 and the object is weak, other information need not be used. In this case, correction of deformed tomographic images is unnecessary. Sequenced luminance value data is reconstructed based on a slightly deformed tomographic image group and their positions and orientations on the reference coordinate system.

Eighth Modification

In the ninth embodiment, a general pointing device such as a pen may be used as a pointing unit in place of the ultrasonic probe 5195. In this case, the position of the contact point between the pointing device and an object on a pointing device coordinate system is calculated and stored in advance, thereby obtaining a point group representing the object surface. The pointing device coordinate system is a coordinate system whose origin is defined at one point on the pointing device, and whose X-, Y-, and Z-axes are defined as three axes that cross at right angles at that origin.

Contact between the pointing device and the object is determined based on a contact sensor attached to the pointing device or the object, as in the fourth modification of other embodiments. The determination may be done based on the measured value of a position and orientation sensor and the shape information of the object, as in the fifth modification of other embodiments. As in the 10th embodiment, a pressure sensor may be attached to the pointing device so as to reconstruct a three-dimensional geometric model using only the measured value of the position and orientation sensor when the contact pressure on the object is weak.

According to this modification, it is possible to reconstruct a three-dimensional geometric model with less influence of object deformation by the pointing device. All or some of the eighth and subsequent embodiments and modifications may be combined as needed.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-087835 filed Mar. 31, 2009, which is hereby incorporated by reference herein in its entirety.

The invention claimed is:

1. An image processing apparatus comprising:
at least one processor; and
a memory, to which the processor is operatively coupled, storing instructions that, when executed by the processor, cause the processor to:
  acquire a tomographic image of an object obtained by an image sensing unit;
  acquire three-dimensional volume data of the object;
  detect an unclear image sensing region on the basis of luminance values within the tomographic image; and
  generate an image by complementing the unclear image sensing region using an image of a slice which is in the three dimensional volume data and which corresponds to the unclear image sensing region,
  wherein a part of a region of interest is detected from the tomographic image using a method based on edge detection and a region behind the detected part of the region of interest is defined as the unclear image sensing region.

2. The image processing apparatus according to claim 1, wherein an image sensing clarity is a value obtained by dividing a sum of differences between a threshold and pixel values of pixels of a selected vertical line sequentially selected from the tomographic image by a product of the threshold and the number of pixels of the selected vertical line.

3. The image processing apparatus according to claim 1, wherein the instructions further cause the image processing apparatus to:
obtain, for each pixel of the tomographic image, a first image sensing clarity that takes a higher value corresponding to a lower pixel value,
obtain, as a second image sensing clarity, a value obtained by dividing a difference between an average pixel value X in a region immediately under the part of the region of interest of the tomographic image and an average pixel value Y in regions adjacent to left and right sides of the region immediately under by the average pixel value Y in the regions adjacent to the left and right sides if $Y>=X$ or a value obtained by subtracting the average pixel value Y in the regions adjacent to the left and right sides from a maximum pixel value that the pixel value can take if $Y<X$, and
compose the tomographic image with the image of the slice by composing, for each pixel, the tomographic image with the image of the slice in accordance with a ratio calculated based on the corresponding first image sensing clarity and the second image sensing clarity.

4. The image processing apparatus according to claim 1, wherein the instructions further cause the image processing apparatus to:
obtain, for each pixel of the tomographic image, an image sensing clarity that takes a higher value corresponding to a lower pixel value, and
compose the tomographic image with the image of the slice by composing, for each pixel, the tomographic image with the image of the slice in accordance with a ratio based on a corresponding image sensing clarity and a corresponding reliability, and
wherein the reliability is a value predetermined for each pixel of the image of the slice and predetermined for each voxel of the three-dimensional volume data used to generate the pixels.

5. The image processing apparatus according to claim 4, wherein the instructions further cause the image processing apparatus to display an image obtained by composing the tomographic image with the image of the slice, and
wherein each pixel of the image obtained by composing the tomographic image is displayed with the image of the slice, in a display form corresponding to a value based on the corresponding image sensing clarity and the corresponding reliability.

6. The image processing apparatus according to claim 1, wherein the instructions further cause the image processing apparatus to display the generated image, and
wherein, when displaying the generated image, the unclear image sensing region and remaining regions are displayed discriminately.

7. The image processing apparatus according to claim 1, wherein the instructions further cause the image processing apparatus to display the generated image, and
wherein, when displaying the generated image, unclear image sensing regions of different types are displayed discriminately.

8. The apparatus according to claim 1, wherein the instructions further cause the image processing apparatus to detect, as the unclear image sensing region, a lacked image region from the tomographic image.

9. The apparatus according to claim 1, wherein the unclear image sensing region is detected on the basis of a relationship between a pixel value of each pixel within the tomographic image and a threshold.

10. The apparatus according to claim 1, wherein the unclear image sensing region is detected on the basis of a relationship between a pixel value of each pixel within the tomographic image and pixel values of surrounding pixels thereof.

11. The apparatus according to claim 1, wherein when pixel values of all pixels within a line is equal to or less than a threshold, the line is defined as the unclear image sensing region.

12. An image processing method comprising:
acquiring a tomographic image of an object obtained by an image sensing unit; acquiring three-dimensional volume data of the object;
detecting an unclear image sensing region on the basis of luminance values within the tomographic image; and
generating an image by complementing the unclear image sensing region using an image of a slice which is in the three dimensional volume data and which corresponds to the unclear image sensing region,
wherein a part of a region of interest is detected from the tomographic image using a method based on edge detection and a region behind the detected part of the region of interest is defined as the unclear image sensing region.

13. An image processing apparatus comprising:
    at least one processor;
    a memory, to which the processor is operatively coupled, storing instructions that, when executed by the processor, cause the processor to:
        acquire a tomographic image of an object obtained by an image sensing unit;
        acquire three-dimensional volume data of the object;
        calculate image sensing clarity for each pixel of the tomographic image on the basis of a pixel value of each pixel of the tomographic image;
        detect an unclear image sensing region on the basis of luminance values within the tomographic image; and
        compose the tomographic image with an image of a slice which is in the three-dimensional volume data and which corresponds to the unclear image sensing region by compositing, for each pixel, the tomographic image with the image of the slice in accordance with a ratio represented by a corresponding image sensing clarity,
    wherein a part of a region of interest is detected from the tomographic image using a method based on edge detection and a region behind the detected part of the region of interest is defined as the unclear image sensing region.

14. The image processing apparatus according to claim 13, wherein the image sensing clarity is a value obtained by dividing a sum of differences between a threshold and pixel values of pixels of a selected vertical line sequentially selected from the tomographic image by a product of the threshold and the number of pixels of the selected vertical line.

15. The image processing apparatus according to claim 13, wherein the instructions further cause the image processing apparatus to:
    obtain, for each pixel of the tomographic image, a first image sensing clarity that takes a higher value corresponding to a lower pixel value,
    obtain, as a second image sensing clarity, a value obtained by dividing a difference between an average pixel value X in a region immediately under the part of the region of interest of the tomographic image and an average pixel value Y in regions adjacent to left and right sides of the region immediately under by the average pixel value Y in the regions adjacent to the left and right sides if Y>=X or a value obtained by subtracting the average pixel value Y in the regions adjacent to the left and right sides from a maximum pixel value that the pixel value can take if Y<X, and
    compose the tomographic image with the image of the slice by composing, for each pixel, the tomographic image with the image of the slice in accordance with a ratio calculated based on the corresponding first image sensing clarity and the second image sensing clarity.

16. The image processing apparatus according to claim 13, wherein the instructions further cause the image processing apparatus to:
    obtain, for each pixel of the tomographic image, an image sensing clarity that takes a higher value corresponding to a lower pixel value, and
    compose the tomographic image with the image of the slice by composing, for each pixel, the tomographic image with the image of the slice in accordance with a ratio based on a corresponding image sensing clarity and a corresponding reliability, and
    wherein the reliability is a value predetermined for each pixel of the image of the slice and predetermined for each voxel of the three-dimensional volume data used to generate the pixels.

17. The apparatus according to claim 16, wherein the instructions further cause the image processing apparatus to display an image obtained by composing the tomographic image with the image of the slice, and
    wherein each pixel of the image obtained by composing the tomographic image with the image of the slice is displayed in a display form corresponding to a value based on the corresponding image sensing clarity and the corresponding reliability.

* * * * *